(12) United States Patent
Thum et al.

(10) Patent No.: US 10,174,353 B2
(45) Date of Patent: Jan. 8, 2019

(54) METHODS OF PRODUCING RHAMNOLIPIDS

(71) Applicant: Evonik Degussa GmbH, Essen (DE)

(72) Inventors: Oliver Thum, Ratingen (DE); Philip Engel, Essen (DE); Christian Gehring, Marl (DE); Steffen Schaffer, Herten (DE); Mirja Wessel, Bochum (DE)

(73) Assignee: Evonik Degussa GmbH, Essen (DE)

( * ) Notice: Subject to any disclaimer, the term of this patent is extended or adjusted under 35 U.S.C. 154(b) by 1 day.

(21) Appl. No.: 15/311,850

(22) PCT Filed: Apr. 27, 2015

(86) PCT No.: PCT/EP2015/059044
§ 371 (c)(1),
(2) Date: Nov. 17, 2016

(87) PCT Pub. No.: WO2015/180907
PCT Pub. Date: Dec. 3, 2015

(65) Prior Publication Data
US 2017/0096695 A1    Apr. 6, 2017

(30) Foreign Application Priority Data
May 26, 2014  (EP) ................... 14169799

(51) Int. Cl.
| | | |
|---|---|---|
| C12P 19/44 | (2006.01) | |
| C12P 7/42 | (2006.01) | |
| C12N 9/10 | (2006.01) | |
| C12N 11/00 | (2006.01) | |
| C12N 15/52 | (2006.01) | |
| A01N 25/30 | (2006.01) | |
| C12N 9/02 | (2006.01) | |
| C12N 9/14 | (2006.01) | |

(52) U.S. Cl.
CPC .............. *C12P 19/44* (2013.01); *A01N 25/30* (2013.01); *C12N 9/0004* (2013.01); *C12N 9/1051* (2013.01); *C12N 9/14* (2013.01); *C12N 15/52* (2013.01); *C12Y 204/01159* (2013.01)

(58) Field of Classification Search
CPC ....... C12P 19/44; C12N 15/63; C12N 9/1051; C12N 9/14; C12N 1/20; C12N 9/0004
USPC ................... 435/174, 252.3, 320.1; 536/23.2
See application file for complete search history.

(56) References Cited

U.S. PATENT DOCUMENTS

| | | |
|---|---|---|
| 4,601,893 A | 7/1986 | Cardinal |
| 5,175,108 A | 12/1992 | Bachmann et al. |
| 5,965,391 A | 10/1999 | Reinscheid et al. |
| 6,013,494 A | 1/2000 | Nakamura et al. |
| 6,136,576 A | 10/2000 | Diaz-Torres et al. |
| 6,238,896 B1 | 5/2001 | Ozaki et al. |
| 8,404,470 B2 | 3/2013 | Thum et al. |
| 8,486,677 B2 | 7/2013 | Thum et al. |
| 8,647,848 B2 | 2/2014 | Hollmann et al. |
| 8,796,000 B2 | 8/2014 | Thum et al. |
| 8,911,982 B2 | 12/2014 | Schaffer et al. |
| 8,980,594 B2 | 3/2015 | Reinecke et al. |
| 9,005,928 B2 | 4/2015 | Schaffer et al. |
| 9,012,227 B2 | 4/2015 | Karau et al. |
| 9,068,211 B2 | 6/2015 | Schaffer et al. |
| 9,085,787 B2 | 7/2015 | Schaffer et al. |
| 9,102,968 B2 | 8/2015 | Schaffer et al. |
| 9,157,108 B2 | 10/2015 | Schaffer et al. |
| 9,243,212 B2 | 1/2016 | Kuppert et al. |
| 9,271,908 B2 | 3/2016 | Allef et al. |
| 9,351,485 B2 | 5/2016 | Giessler-Blank et al. |
| 9,388,439 B2 | 7/2016 | Schaffer et al. |
| 9,434,755 B2 | 9/2016 | Schilling et al. |
| 9,580,720 B2 | 2/2017 | Schaffer et al. |
| 9,719,117 B2 | 8/2017 | Schaffer et al. |
| 2011/0065801 A1 | 3/2011 | Hollmann et al. |
| 2013/0130319 A1 | 5/2013 | Schaffer et al. |

(Continued)

FOREIGN PATENT DOCUMENTS

| | | |
|---|---|---|
| DE | 100 31 999 | 4/2001 |
| DE | 10 1012 20136 | 8/2013 |

(Continued)

OTHER PUBLICATIONS

Devos et al., Proteins: Structure, Function and Genetics, 2000, vol. 41: 98-107.*

(Continued)

*Primary Examiner* — Robert B Mondesi
*Assistant Examiner* — Mohammad Y Meah
(74) *Attorney, Agent, or Firm* — Law Office of: Michael A. Sanzo, LLC

(57) ABSTRACT

The present invention relates to a method of preparing at least one rhamnolipid comprising:

contacting a recombinant cell with a medium containing a carbon source; and culturing the cell under suitable conditions for preparation of the rhamnolipid from the carbon source by the cell, wherein the recombinant cell has been genetically modified such that, compared to the wild-type of the cell, the cell has an increased activity of at least one of the enzymes $E_1$, $E_2$ and $E_3$, wherein the enzyme $E_1$ is an α/β hydrolase, the enzyme $E_2$ is a rhamnosyltransferase I and the enzyme $E_3$ is a rhamnosyl-transferase II, and wherein the carbon source is a $C_4$ molecule.

20 Claims, 1 Drawing Sheet
Specification includes a Sequence Listing.

(56) References Cited

U.S. PATENT DOCUMENTS

| | | |
|---|---|---|
| 2014/0178948 A1 | 6/2014 | Schaffer et al. |
| 2014/0235561 A1 | 8/2014 | Blank et al. |
| 2014/0296168 A1 | 10/2014 | Schilling et al. |
| 2015/0203443 A1 | 7/2015 | Klosterman et al. |
| 2015/0247151 A1 | 9/2015 | Schaffer et al. |
| 2016/0045424 A1 | 2/2016 | Schwab et al. |
| 2016/0326555 A1 | 11/2016 | Engel et al. |
| 2017/0130248 A1 | 5/2017 | Reinecke et al. |
| 2018/0066297 A1 | 3/2018 | Haas et al. |

FOREIGN PATENT DOCUMENTS

| | | |
|---|---|---|
| EP | 2 573 172 | 3/2013 |
| GB | 1009370 | 11/1965 |
| JP | H 10229891 | 2/1998 |
| WO | WO 96/15246 | 5/1996 |
| WO | WO 2011/154503 | 12/2011 |
| WO | WO 2015/176922 | 11/2015 |
| WO | WO 2015/180907 | 12/2015 |

OTHER PUBLICATIONS

Whisstock et al., (Quarterly Reviews of Biophysics 2003, vol. 36 (3): 307-340.*

Witkowski et al., (Biochemistry 38:11643-11650, 1999.*

Kisselev L., (Structure, 2002, vol. 10: 8-9.*

International Search Report for corresponding international application PCT/EP2015/059044 filed Apr. 27, 2015.

Written Opinion of the International Searching Authority for corresponding application PCT/EP2015/059044 filed Apr. 27, 2015.

International Preliminary Report on Patentability for corresponding international application PCT/EP2015/059044 filed Apr. 27, 2015.

European Search Report for priority application EP 14 16 9799 completed Oct. 28, 2014.

GenBank: CAB54050.1, :alkane-1 monooxygenase (plasmid) [*Pseudomonas putida*].

Eggink, et al., "Rubredoxin reductase of *Pseudomonas oleovorans*, Structural relationship to other flavorprotein oxidoreductases based on one NAD and two FAD fingerprints," *J. Mol. Biol.* 212:135-142 (Mar. 1990).

Johnson, et al., "Propane and n-Butane Oxidation by *Pseudomonas putida* GPo1," *Applied and Environmental Microbiology* 72(1)950-952 (Jan. 2006).

Kok, et al., "The *Pseudomonas oleovorans* Alkane Hydroxylase Gene," *J. Biol. Chem.* 264(10):5435-5441 (Apr. 1989).

Kok, et al., "The *Pseudomonas oleovorans* alkBAC Operon Encodes Two Structurally Related Rubredoxins and an Aldehyde Dehydrogenase," *J. Biol. Chem.* 264(10):5442-5451 (Apr. 1989).

Leitermann, et al., *Handbook of Hydrocarbon and Lipid Microbiology*, pp. 3037-3051 (2010).

Müller, et al., "*Pseudomonas aeruginosa* PAO1 as a model for rhamnolipid production in bioreactor systems," *Appl. Microbiol. Biotechnol.* 87(1):167-174 (Mar. 2010).

Panke, et al., :An Alkane-Responsive Expression System for the Production of Fine Chemicals, *Applied and Environmental Microbiology* 65(6):2324-2332 (Jun. 1999).

Schleheck, et al., "*Pseudomonas aeruginosa* PAO1 Preferentially Grows as Aggregates in Liquid Batch Cultures and Disperses upon Starvation," *PLOS One* 4(5): 1-15, (May 2009).

Sha, et al., "The addition of ethanol as defoamer in fermentation of rhamnolipids," *J. Chem. Technol. Biotechnol.* 87:368-373 (Jan. 2012).

Van Beilen, et al., "DNA sequence determination and functional characterization of the OCT-plasmid-encoded alkJKL genes of *Pseudomonas oleovorans*," *Mol Microbiol* 6:3121-3136 (Nov. 1992).

U.S. Appl. No. 15/312,627, filed Nov. 19, 2016, Reinecke, et al.

International Search Report for PCT/EP2016/053222 filed Feb. 16, 2016, corresponding to copending U.S. Appl. No. 15/551,904.

Written Opinion of the International Searching Authority for PCT/EP2016/053222 filed Feb. 16, 2016 corresponding to copending U.S. Appl. No. 15/551,904.

International Preliminary Report on Patentability for PCT/EP2016/053222 filed Feb. 16, 2016 corresponding to copending U.S. Appl. No. 15/551,904.

European Search Report for priority application EP 15 15 5706 completed Aug. 27, 2015 coresponding to PCT/EP2016/053222 filed Feb. 16, 2016.

Benson et al., "Plasmid-Determined Alcohol Dehydrogenase Activity in Alkane-Utilizing Strains of *Pseudonomas putida*," *Journal of Bacteriology* 126(2):794-798 (May 1976).

Choi, et al., "Metabolic relationship between polyhydroxyalkanoic acid and rhamnolipid synthesis in *Pseudomonas aeruginosa*: Comparative $^{13}$C NMR analysis of the products in wild-type and mutants," *Journal of Biotechnology* 151(1):30-42 (Jan. 2011).

Iwasaki, et al., "Transformation of *Pseudomonas putida* by Electroporation," *Biosci. Biotech. Biochem.* 58(5):851-854 (1994).

Wittgens, et al., "Growth independent rhamnolipid production from glucose using the non-pathogenic *Pseudomonas putida* KT2440," *Microbial Cell Factories* 10(1):80 (Oct. 2011).

Database UniProt [Online]; retrieved from EBI accession No. UNIPROT A6V1U7; SubName: Full=Rhamnosyltransferase chain B (Aug. 21, 2007).

Database UniProt [Online]; retrieved from EBI accession No. UNIPROT D2EDQ2; SubName: Full=Rhamnosyltransferase-2 (Feb. 9, 2010).

Database UniProt [Online]; retrieved from EBI accession No. UNIPROT U8MP69; SubName: Full=Rhamnosyltransferase chain B (Jan. 22, 2014).

Database UniProt [Online]; retrieved from EBI accession No. UNIPROT X6YS63; SubName: Full=Rhamnosyltransferase 2 (Jun. 11, 2014).

Database UniProt [Online]; retrieved from EBI accession No. UNIPROT A6V1U6; SubName: Full=Rhamnosyltransferase chain A (Aug. 21, 2007).

Database UniProt [Online]; retrieved from EBI accession No. UNIPROT D2EDM3; SubName: Full=Rhamnosyltransferase-1 (Feb. 9, 2010).

U.S. Appl. No. 15/551,904, filed Aug. 18, 2017, US 2018/0066297 A1, Mar. 8, 2018, Haas, et al.

* cited by examiner

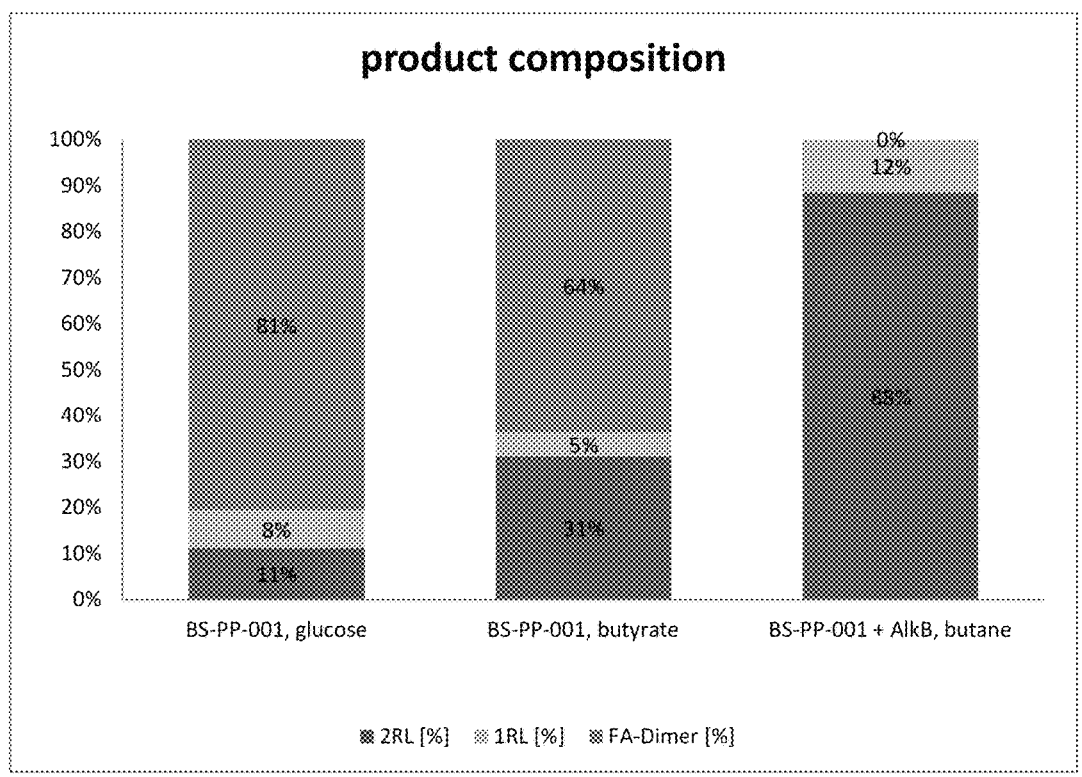

METHODS OF PRODUCING RHAMNOLIPIDS

CROSS REFERENCE TO RELATED APPLICATIONS

The present application is US national stage of international application PCT/EP2015/059044, which had an international filing date of Apr. 27, 2015, and which was published in English on Dec. 3, 2015. Priority is claimed to European application EP 14169799.5, filed on May 26, 2014. The contents of the priority application is hereby incorporated by reference in its entirety.

FIELD OF THE INVENTION

The present invention relates to methods and cells for producing at least one rhamnolipid from a carbon source.

BACKGROUND OF THE INVENTION

There is a general demand in the market for biodegradable surfactants that are produced from renewable raw materials as a suitable alternative to the currently available surfactants which are obtained from petrochemical raw materials. This demand is in particular accentuated with the foreseeable shortage of petrochemical raw materials and increasing demand for surfactants. Rhamnolipids are at least one example of such a surfactant. Rhamnolipids represent an economically interesting class because they may potentially replace conventional surfactants made from petroleum or products thereof, and thus invariably improve the environmental performance of the resulting formulations.

These rhamnolipids comprise at least one monorhamnosyl lipid or two rhamnose radicals (dirhamnosyl lipids) and one or two 3-hydroxy fatty acid residues (Handbook of Hydrocarbon and Lipid Microbiology, 2010). They have surface-active properties, which are needed in all sorts of applications for use as a surfactant (see Leitermann et al., 2009). In particular, rhamnolipids, may be employed to a large extent as surfactants in household, cleaning, cosmetic, food processing, pharmaceutical, plant protection and other applications.

The currently used methods to produce these rhamnolipids employ wild-type isolates of various human and animal pathogenic bacteria, particularly members of the genera *Pseudomonas* and *Burkholderia*, (Handbook of Hydrocarbon and Lipid Microbiology, 2010). The fact that these pathogenic organisms are capable of causing diseases to the consumer considerably reduces the customer's acceptance for these conventionally produced rhamnolipids. Further, higher safety requirements also increase the production costs owing to increased capital expenditure and possibly additional production steps. Since the products in which these rhamnolipids are used are mostly high volume chemicals which can be produced at very low costs, the rhamnolipids must also be able to be produced at costs as low as possible, without health risks for the customer and with defined properties as far as possible.

The current methods available for production of rhamnolipids include the use of these pathogenic organisms and vegetable oils as the sole or co-substrate (*Handbook of Hydrocarbon and Lipid Microbiology*, 2010). Vegetable oils, however, are comparatively expensive raw materials in comparison to other carbon sources, such as, for example, glucose, sucrose or polysaccharides such as, for example, starch, cellulose and hemicellulose, glycerol, CO, $CO_2$ or $CH_4$. Rhamnolipids are also produced by non-pathogenic organisms using carbon sources, such as, for example, glucose, sucrose or polysaccharides as taught in WO2012013554A1.

However, there still lies a need to produce rhamnolipids (in particular, monorhamnosyl lipid and/or dirhamnosyl lipids) efficiently (i.e. inexpensively and, from the health point of view, safely) and in more than adequate amounts using non-pathogenic organisms and an alternative renewable raw material.

DESCRIPTION OF THE INVENTION

According to one aspect, the present invention relates to a method that may be capable of solving the problems present in the state of the art. In particular, the present invention relates to a method of producing at least one rhamnolipid by culturing a recombinant cell in the presence of at least one carbon source wherein the carbon source is at least one $C_4$ molecule with exactly 4 carbon atoms. The recombinant cell comprises increased activity of at least one of the enzymes α/β hydrolase, rhamnosyltransferase I or rhamnosyl-transferase II compared to the wild-type of the cell. This method may especially be advantageous as it may allow for high selective production of monorhamnosyl lipids and/or dirhamnosyl lipids with a reduction in the amount of undesirable by-products and intermediates produced. For example, there may at least be less intermediates such as dimers of β-Hydroxy fatty acids (fatty acid dimers) formed according to any aspect of the present invention compared to the currently available methods.

Further advantages of the method according to any aspect of the present invention include but are not limited to the fact that organisms can be utilised that are non-pathogenic and simple to culture. A further advantage may include the fact that with the method according to any aspect of the present invention, it may not be necessary that oils and simple carbohydrate substrates (e.g. glucose, fructose or sucrose) are the only substrate or co-substrate. According to any aspect of the present invention, another advantage may be that rhamnolipids having defined and modulatable properties can be produced. Also, specifically, dirhamnosyl lipids can be produced. A further advantage may be that rhamnolipids can be produced with higher space-time and carbon yields than with cells without enhancement of these activities.

According to any aspect of the present invention, rhamnolipids and/or rhamnolipid mixtures thereof that can be produced using any aspect of the present invention may be likewise a subject of the present invention. The rhamnolipids and mixtures that can be produced according to any aspect of the present invention can advantageously be employed at least in cleaning or care agents, in cosmetic, dermatological or pharmaceutical formulations as well as in plant protection formulations, surfactant concentrates and the like.

The term "care agents" is understood here as meaning a formulation that fulfils the purpose of maintaining an article in its original form, reducing or avoiding the effects of external influences (e.g. time, light, temperature, pressure, pollution, chemical reaction with other reactive compounds coming into contact with the article and the like) and aging, pollution, material fatigue, and/or even for improving desired positive properties of the article. An example of desired positive properties of the article may include features such as an improved hair gloss or a greater elasticity of the article and the like.

"Plant protection formulations" are to be understood herein as meaning those formulations that by the nature of their preparation are used for plant protection. This is in particular the case if at least one compound from the group consisting of herbicides, fungicides, insecticides, acaricides, nematicides, protective substances against bird damage, plant nutrients and soil structure-improving agents is contained in the formulation.

The rhamnolipids produced according to any aspect of the present invention may be used as a component of care and cleaning agents that are used in housekeeping, industry, in particular on hard surfaces, leather and/or textiles.

According to one aspect of the present invention, there is provided at least one method of preparing at least one rhamnolipid comprising:

contacting a recombinant cell with a medium containing a carbon source; and culturing the cell under suitable conditions for preparation of the rhamnolipid from the carbon source by the cell, wherein the recombinant cell has been genetically modified such that, compared to the wild-type of the cell, the cell has an increased activity of at least one of the enzymes $E_1$, $E_2$ and $E_3$, wherein the enzyme $E_1$ is an $\alpha/\beta$ hydrolase, the enzyme $E_2$ is a rhamnosyltransferase I and the enzyme $E_3$ is a rhamnosyl-transferase II, and wherein the carbon source is a $C_4$ molecule.

According to another aspect of the present invention, there is provided a cell which is able to form at least one rhamnolipid from a $C_4$ molecule, wherein the cell has been genetically modified such that, compared to the wild-type of the cell, the cell has an increased activity of the enzyme oxidoreductase and at least one of the enzymes $E_1$, $E_2$ and $E_3$, wherein the enzyme $E_1$ is alp hydrolase, the enzyme $E_2$ is rhamnosyltransferase I and the enzyme $E_3$ is rhamnosyl-transferase II.

More in particular, the cells according to any aspect or the present invention may be able to form rhamnolipids and compared to their wild-type have increased activity of at least one gene product or homologs of the gene products rhlA, rhlB and rhlC. At least in one example, the genes rhlA, rhlB and rhlC from *Pseudomonas aeruginosa* may be introduced into GRAS organisms (generally regarded as save) (as described in WO2012013554A1) to produce rhamnolipids from $C_4$ molecules. In one specific example the cell according to any aspect of the present invention may be *P. putida* of the strain KT2440.

In particular, the $C_4$ molecule referred to herein may be a structure comprising C, H and/or O. In particular, the $C_4$ molecule may be any compound comprising exactly 4 carbon atoms (i.e. no more or no less than 4 carbon atoms in each unit) in the structure of the compound. The "$C_4$ molecule" according to any aspect of the present invention refers to an organic compound comprising exactly four C atoms and a variable number of H atoms depending on the other atoms found in the structure of the compound with 4 carbon atoms. The $C_4$ molecule may also comprise O atoms. In particular, the $C_4$ molecule according to any aspect of the present invention may be butane and the oxidised products of butane. The oxidised products of butane include at least 1-butanol, 2-butanol, 1-butanal, butanone and butyric acid. In particular, the $C_4$ molecule may be selected from the group consisting of butane, 1-butanol, 2-butanol, 1-butanal, butanone, butyric acid (butyrates) and combinations thereof. The $C_4$ molecule may also be a tetrose.

More in particular, the $C_4$ molecule used according to any aspect of the present invention may only be one type of $C_4$ molecule (i.e. only butane, 1-butanol, 2-butanol, 1-butanal, butanone or butyric acid). In one example, $C_4$ molecule used may be a combination of any of the $C_4$ molecules selected from the group consisting of butane, 1-butanol, 2-butanol, 1-butanal, butanone and butyric acid. For example, the $C_4$ molecule according to any aspect of the present invention may be a combination of butane and 1-butanol, butane and 2-butanol, butane and 1-butanal, butane and butanone, butane and butyric acid and the like. In one example, there may be at least 3, 4, 5 or 6 different $C_4$ molecules used as a carbon source according to any aspect of the present invention. In another example, there may be a combination of butane, 1-butanol and butyric acid used as the $C_4$ molecule according to any aspect of the present invention. In another example, tetrose may be used alone or in combination with butane and butane oxidation products as the carbon source according to any aspect of the present invention.

The medium used according to any aspect of the present invention comprises at least one carbon source. The carbon source in the medium may at least be a $C_4$ molecule. In particular, the carbon source in the medium may consist essentially of or comprise substantially a $C_4$ molecule. In particular, the total amount of $C_4$ molecules is at least or equal to 20%, 40%, 50%, 60% or 70% by weight of the total carbon content in the medium of $C_4$ molecules carbon source in the total medium. More in particular, the total amount $C_4$ molecule is at least or equal to 50%, 70% or 80% by weight of the carbon source in the medium. Even more in particular, the $C_4$ molecule may at least be or equal to 90% or about 100% by weight of the carbon source in the medium.

In one example, the medium may comprise a second carbon source. In particular, the carbon source may be carbohydrates such as, for example, glucose, sucrose, arabinose, xylose, lactose, fructose, maltose, molasses, starch, cellulose and hemicellulose, vegetable and animal oils and fats such as, for example, soybean oil, safflower oil, peanut oil, hempseed oil, jatropha oil, coconut fat, calabash oil, linseed oil, corn oil, poppyseed oil, evening primrose oil, olive oil, palm kernel oil, palm oil, rapeseed oil, sesame oil, sunflower oil, grapeseed oil, walnut oil, wheat germ oil and coconut oil, fatty acids, such as, for example, caprylic acid, capric acid, lauric acid, myristic acid, palmitic acid, palmitoleic acid, stearic acid, arachidonic acid, behenic acid, oleic acid, linoleic acid, linolenic acid, gamma-linolenic acid and its methyl or ethyl ester as well as fatty acid mixtures, mono-, di- and triglycerides containing any fatty acids mentioned above, alcohols such as, for example, glycerol, ethanol and methanol, hydrocarbons such as methane, carbon-containing gases and gas mixtures, such as CO, $CO_2$, synthesis or flue gas, amino acids such as L-glutamate or L-valine or organic acids such as, for example, acetic acid. These substances can be used individually or as a mixture. Carbohydrates, in particular monosaccharides, oligosaccharides or polysaccharides, as the carbon source as is described in U.S. Pat. No. 6,01,494 and U.S. Pat. No. 6,136,576 as well as of hydrocarbons, in particular of alkanes, alkenes and alkynes as well as the monocarboxylic acids derived therefrom and the mono-, di and triglycerides derived from these monocarboxylic acids, as well as of glycerol and acetate, may be used. Mono-, di- and triglycerides containing the esterification products of glycerol with caprylic acid, capric acid, lauric acid, myristic acid, palmitic acid, palmitoleic acid, stearic acid, arachidonic acid, behenic acid, oleic acid, linoleic acid, linolenic acid and/or gamma-linolenic acid may be used.

It is a great advantage according to any aspect of the present invention that the cells may be able to form rhamnolipids from the simplest carbon sources such as butane, such that a provision of longer-chain carbon sources in the medium according to any aspect of the present invention may not be necessary. This may be especially advantageous in the case of lack of availability in the medium according to any aspect of the present invention of detectable amounts of carboxylic acids having a chain length of greater than six carbon atoms or esters or glycerides derivable from these.

Basic compounds such as sodium hydroxide, potassium hydroxide, ammonia or ammonia water or acidic compounds such as phosphoric acid or sulfuric acid may be suitably employed in the medium for pH control of the culture. Anti-foam agents such as, for example, fatty acid polyglycol esters can be employed for the control of foam development. Suitable selectively acting substances such as, for example, antibiotics can be added to the medium for maintaining the stability of plasmids. To maintain aerobic conditions, oxygen or oxygen-containing gas mixtures such as, for example, air may be incorporated into the culture.

The temperature of the culture is usually more than or equal to 20° C., 25° C., it can also be more than or equal to 40° C., wherein advantageously a culturing temperature of at least or equal to 95° C., particularly at least or equal to 90° C. and more particularly at least or equal to 80° C. may be used.

A skilled person would understand what constitutes suitable conditions for culturing the recombinant cells according to any aspect of the present invention to produce rhamnolipids from at least a $C_4$ molecule.

Using basic methods known in the art, a skilled person would be capable of varying the conditions in the medium to suit the relevant cell used according to any aspect of the present invention.

In the method according to any aspect of the present invention, the rhamnolipids formed by the cells can optionally be isolated from the cells and/or the medium. All methods known in the art for isolation of low molecular weight substances from complex compositions may be applied. For example, methods such as filtration, extraction, adsorption (chromatography), crystallization and the like may be used in the product phase.

The isolated product in the product phase may also comprise other unwanted residues of biomass and various impurities, such as oils, fatty acids and other nutrient media constituents. The separation of these impurities and the like may take place in a solvent-free process. Thus, for example, the isolated product may first be diluted with water to facilitate the adjustment of the pH. The product and aqueous phases may then be homogenized by converting the rhamnolipids into a water-soluble form by lowering or raising the pH with acids or alkalis respectively. The solubility of the rhamnolipids in the aqueous phase may be assisted by incubation of the reaction mixture at higher temperatures, e.g. at 60 to 90° C., and/or with constant mixing. By subsequent raising or lowering of the pH by alkalis or acids the rhamnolipids can then again be converted into a water-insoluble form, such that they can easily be separated from the aqueous phase. The product phase can then be washed once or several times with water to remove the water-soluble impurities.

OH residues can be separated off, for example by extraction by means of suitable solvents advantageously by means of organic solvents. An alkane such as, for example, n-hexane and the like may be used as a solvent.

The separation of the product from the aqueous phase can be effected alternatively to the solvent-free process described above using a suitable solvent, e.g. an ester such as, for example, ethyl acetate, butyl acetate and the like.

These extraction steps may be carried out in any desired sequence. A skilled person would be able to easily vary the sequence of steps and/or the solvents used to be suitable for the cell and the rhamnolipid to be extracted.

In another example, solvents may be employed in the extraction of the rhamnolipids produced according to any aspect of the present invention. In particular, organic solvents may be used. More in particular, n-Pentanol may be used as a solvent. A distillation, for example, takes place for the removal of the solvent. Subsequently, the lyophilized product can be further purified, for example by means of chromatographic methods. By way of example, precipitation by means of suitable solvents, extraction by means of suitable solvents, complexation, for example by means of cyclodextrins or cyclodextrin derivatives, crystallization, purification or isolation by means of chromatographic methods or conversion of the rhamnolipids into easily separable derivatives may be employed.

The recombinant cell employed according to any aspect of the present invention, has been genetically modified such that, compared to the wild-type of the cell, the cell has an increased activity of at least one of the enzymes $E_1$, $E_2$ and $E_3$, wherein the enzyme $E_1$ is an α/β hydrolase, the enzyme $E_2$ is a rhamnosyl-transferase I and the enzyme $E_3$ is a rhamnosyl-transferase II. The recombinant cell used according to any aspect of the present invention may be made according to the method disclosed in WO2012013554A1.

In particular, in the cell according to any aspect of the present invention, the enzyme $E_1$ may be able to catalyze the conversion of 3-hydroxyalkanoyl-ACP via 3-hydroxyalkanoyl-3-hydroxyakanoic acid-ACP to hydroxyalkanoyl-3-hydroxyalkanoic acid, the enzyme $E_2$ may be a rhamnosyl-transferase I and may be able to catalyze the conversion of dTDP-rhamnose and 3-hydroxyalkanoyl-3-hydroxyalkanoate to a-L-rhamnopyranosyl-3-hydroxyakanoyl-3-hydroxyakanoate and the enzyme $E_3$ may be a rhamnosyltransferase II and may be able to catalyze the conversion of dTDP-rhamnose and a-L-rhamnopyranosyl-3-hydroxyalkanoyl-3-hydroxy-alkanoate to a-L-rhamnopyranosyl-(1-2)-a-L-rhamnopyranosyl-3-hydroxyakanoyl-3-hydroxyalkanoate, wherein these enzymes $E_1$, $E_2$ and $E_3$ may be selected from the group consisting of:

at least one enzyme $E_1$ comprising an amino acid sequence selected from the group consisting of SEQ ID NO:2, SEQ ID NO:3, SEQ ID NO:4, SEQ ID NO:5, SEQ ID NO:6 and fragments thereof; at least one enzyme $E_2$ comprising an amino acid sequence selected from the group consisting of SEQ ID NO:7, SEQ ID NO:8, SEQ ID NO:9, SEQ ID NO:10, SEQ ID NO:11 and fragments thereof, and at least one enzyme $E_3$ comprising an amino acid sequence selected from the group consisting of SEQ ID NO:12, SEQ ID NO:13, SEQ ID NO:14, SEQ ID NO:15, and fragments thereof. The fragment with respect to any one of the enzymes $E_1$, $E_2$, or $E_3$ may comprise a polypeptide sequence in which up to 25% of the amino acid radicals are modified by deletion, insertion, substitution or a combination thereof compared to the sequence of the respective enzyme and the fragment comprises at least 10% of the enzymatic activity of the respective enzyme.

In particular, the enzyme $E_1$ in the cell according to any aspect of the present invention, may be selected from the group consisting of:

an enzyme $E_{1a}$ comprising a polypeptide sequence SEQ ID NO:2 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:2 by deletion, insertion, substitution or a combination thereof and that still has at least 10%, 50%, 80%, in particular more than 90% of the enzymatic activity of the enzyme having the reference sequence SEQ ID NO:2, wherein enzymatic activity for an enzyme $E_{1a}$ may be understood as meaning the ability to convert 3-hydroxydecanoyl-ACP via 3-hydroxydecanoyl-3-hydroxydecanoic add-ACP to hydroxydecanoyl-3-hydroxydecanoic acid, an enzyme $E_{1b}$ comprising a polypeptide sequence SEQ ID NO:3 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:3 by deletion, insertion, substitution or a combination thereof and that still has at least 10%, 50%, 80%, in particular more than 90% of the enzymatic activity of the enzyme having the reference sequence SEQ ID NO:3, wherein enzymatic activity for an enzyme $E_{1b}$ may be understood as meaning the ability to convert 3-hydroxydecanoyl-ACP via 3-hydroxydecanoyl-3-hydroxydecanoic add-ACP to hydroxydecanoyl-3-hydroxydecanoic acid, an enzyme $E_{1c}$ comprising a polypeptide sequence SEQ ID NO:4 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:4 by deletion, insertion, substitution or a combination thereof and that still has at least 10%, 50%, 80%, in particular more than 90% of the enzymatic activity of the enzyme having the reference sequence SEQ ID NO:4, wherein enzymatic activity for an enzyme $E_{1c}$ may be understood as meaning the ability to convert 3-hydroxydecanoyl-ACP via 3-hydroxydecanoyl-3-hydroxydecanoic acid-ACP to hydroxydecanoyl-3-hydroxydecanoic acid, an enzyme $E_{1d}$ comprising a polypeptide sequence SEQ ID NO:5 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:5 by deletion, insertion, substitution or a combination thereof and that still has at least 10%, 50%, 80%, in particular more than 90% of the enzymatic activity of the enzyme having the reference sequence SEQ ID NO:5, wherein enzymatic activity for an enzyme $E_{1d}$ may be understood as meaning the ability to convert 3-hydroxydecanoyl-ACP via 3-hydroxydecanoyl-3-hydroxydecanoic add-ACP to hydroxydecanoyl-3-hydroxydecanoic acid, and an enzyme $E_{1e}$ comprising a polypeptide sequence SEQ ID NO:6 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:6 by deletion, insertion, substitution or a combination thereof and that still has at least 10%, 50%, 80%, in particular more than 90% of the enzymatic activity of the enzyme having the reference sequence SEQ ID NO:6, wherein enzymatic activity for an enzyme $E_{1e}$ may be understood as meaning the ability to convert 3-hydroxydecanoyl-ACP via 3-hydroxydecanoyl-3-hydroxydecanoic add-ACP to hydroxydecanoyl-3-hydroxydecanoic acid.

In particular, the enzyme $E_2$ used in the cell according to any aspect of the present invention may be selected from the group consisting of:

an enzyme $E_{2a}$ having polypeptide sequence SEQ ID NO:7 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:7 by deletion, insertion, substitution or a combination thereof and that still has at least 10%, 50%, 80%, in particular more than 90% of the enzymatic activity of the enzyme having the reference sequence SEQ ID NO:7, wherein enzymatic activity for an enzyme $E_{2a}$ may be understood as meaning the ability preferably to convert dTDP-rhamnose and 3-hydroxydecanoyl-3-hydroxydecanoic acid to a-L-rhamnopyranosyl-3-hydroxydecanoyl-3-hydroxydecanoic acid, an enzyme $E_{2b}$ having polypeptide sequence SEQ ID NO:8 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:8 by deletion, insertion, substitution or a combination thereof and that still has at least 10%, 50%, 80%, in particular more than 90% of the enzymatic activity of the enzyme having the reference sequence SEQ ID NO:8, wherein enzymatic activity for an enzyme $E_{2b}$ may be understood as meaning the ability preferably to convert dTDP-rhamnose and 3-hydroxydecanoyl-3-hydroxydecanoic acid to a-L-rhamnopyranosyl-3-hydroxydecanoyl-3-hydroxydecanoic acid, an enzyme $E_{2c}$ having polypeptide sequence SEQ ID NO:9 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:9 by deletion, insertion, substitution or a combination thereof and that still has at least 10%, 50%, 80%, in particular more than 90% of the enzymatic activity of the enzyme having the reference sequence SEQ ID NO:9, wherein enzymatic activity for an enzyme $E_{2d}$ may be understood as meaning the ability preferably to convert dTDP-rhamnose and 3-hydroxydecanoyl-3-hydroxydecanoic acid to a-L-rhamnopyranosyl-3-hydroxydecanoyl-3-hydroxydecanoic acid, an enzyme $E_{2d}$ having polypeptide sequence SEQ ID NO:10 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:10 by deletion, insertion, substitution or a combination thereof and that still has at least 10%, 50%, 80%, in particular more than 90% of the enzymatic activity of the enzyme having the reference sequence SEQ ID NO:10, wherein enzymatic activity for an enzyme $E_{2d}$ may be understood as meaning the ability preferably to convert dTDP-rhamnose and 3-hydroxydecanoyl-3-hydroxydecanoic acid to a-L-rhamnopyranosyl-3-hydroxydecanoyl-3-hydroxydecanoic acid, and an enzyme $E_{2e}$ having polypeptide sequence SEQ ID NO: 11 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO: 11 by deletion, insertion, substitution or a combination thereof and that still has at least 10%, 50%, 80%, in particular more than 90% of the enzymatic activity of the enzyme having the reference sequence SEQ ID NO: 11, wherein enzymatic activity for an enzyme $E_{2e}$ may be understood as meaning the ability preferably to convert dTDP-rhamnose and 3-hydroxydecanoyl-3-hydroxydecanoic acid to a-L-rhamnopyranosyl-3-hydroxydecanoyl-3-hydroxydecanoic acid.

In particular, the enzyme $E_3$ used in the cell according to any aspect of the present invention may be selected from the group consisting of:

an enzyme $E_{3a}$ having polypeptide sequence SEQ ID NO:12 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:12 by deletion, insertion, substitution or a combination thereof and that still has at least 10%, 50%, 80%, in particular more than 90% of the enzymatic activity of the enzyme having the reference sequence SEQ ID NO:12, wherein enzymatic activity for an enzyme $E_{3a}$ may be understood as meaning the ability preferably to convert dTDP-rhamnose and a-L-rhamnopyranosyl-3-hydroxydecanoyl-3-hydroxydecanoic acid to a-L-rhamnopyranosyl-(1-2)-a-L-rhamnopyranosyl-3-hydroxydecanoyl-3-hydroxydecanoic acid, an enzyme $E_{3b}$ having polypeptide sequence SEQ ID NO:13 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:13 by deletion, insertion, substitution or a combination thereof and that still has at least 10%, 50%, 80%, in particular more than 90% of the enzymatic activity of the enzyme having the reference sequence SEQ ID NO:13, wherein enzymatic activity for an enzyme $E_{3b}$ may be understood as meaning the ability preferably to convert dTDP-rhamnose and a-L-rhamnopyranosyl-3-hydroxydecanoyl-3-hydroxydecanoic acid to a-L-rhamnopyranosyl-(1-2)-a-L-rhamnopyranosyl-3-hydroxydecanoyl-3-hydroxydecanoic acid, an enzyme $E_{3d}$ having polypeptide sequence SEQ ID NO:14 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:14 by deletion, insertion, substitution or a combination thereof and that still has at least 10%, 50%, 80%, in particular more than 90% of the enzymatic activity of the enzyme having the reference sequence SEQ ID NO:14, wherein enzymatic activity for an enzyme $E_{3c}$ may be understood as meaning the ability preferably to convert dTDP-rhamnose and a-L-rhamnopyranosyl-3-hydroxydecanoyl-3-hydroxydecanoic acid to a-L-rhamnopyranosyl-(1-2)-a-L-rhamnopyranosyl-3-hydroxydecanoyl-3-hydroxydecanoic acid, and an enzyme $E_{3d}$ having polypeptide sequence SEQ ID NO:15 or having a polypeptide sequence in which up to 25%, 20%, 15% in particular up to 10, 9, 8, 7, 6, 5, 4, 3, 2, 1% of the amino acid radicals are modified compared to the reference sequence SEQ ID NO:15 by deletion, insertion, substitution or a combination thereof and that still has at least 10%, 50%, 80%, in particular more than 90% of the enzymatic activity of the enzyme having the reference sequence SEQ ID NO:15, wherein enzymatic activity for an enzyme $E_{3d}$ may be understood as meaning the ability preferably to convert dTDP-rhamnose and a-L-rhamnopyranosyl-3-hydroxydecanoyl-3-hydroxydecanoic acid to a-L-rhamnopyranosyl-(1-2)-a-L-rhamnopyranosyl-3-hydroxydecanoyl-3-hydroxydecanoic acid.

A skilled person would understand that the activities indicated above for the enzymes $E_{1a}$ to $E_{3b}$ are only special exemplary choices of a broader spectrum of activities of these enzymes; the respective activity mentioned is that for which a reliable measuring method is available in the case of a given enzyme. Thus, it is obvious that an enzyme with a substrate having an unbranched, saturated $C_{10}$-alkyl radical may also be able to convert those substrates that contain a $C_6$- or $C_{16}$-alkyl radical, which can optionally also be branched or unsaturated.

The recombinant cell according to any aspect of the present invention may also be genetically modified such that compared to the wild-type of the cell, the cell has an increased activity of enzyme, oxidoreductase. In particular, the cell may be genetically modified such that the cell has increased activity of $E_1$, $E_2$ or $E_3$ or combinations thereof and oxidoreductase. More in particular, the cells may have increased activity of $E_1$, $E_2$, $E_3$ and oxidoreductase. In one example, the cells have increased activity of $E_1$ and $E_2$ and oxidoreductase, or $E_1$ and $E_3$ and oxidoreductase, or $E_2$ and $E_3$ and oxidoreductase.

The oxidoreductase may be an alkB-type oxidoreductase. This class of oxidoreductases, alkB, are redox proteins from the *Pseudomonas putida* AlkBGT system, dependent on two auxiliary polypeptides, alkG and alkT. AlkT is a FAD-dependent rubredoxin reductase transferring electrons from NADH to alkG. AlkG is a rubredoxin, an iron-containing redox protein functioning as a direct electron donor to alkB. In one particular example, the alkB-type oxidoreductase is alkB from *Pseudomonas putida* Gpo1 (accession number: CAB54050.1 (version 1), SEQ ID NO:1, any accession number used in the application refers to the respective sequence from the Genbank database run by the NCBI, wherein the release referred to is the one available online on the 4 Apr. 2014).

The enzyme alkB-type oxidoreductase has polypeptide sequence SEQ ID NO:1 or has a polypeptide sequence in which up to 25%, 20%, 15% in particular up to 10, 9, 8, 7, 6, 5, 4, 3, 2, 1% of the amino acid radicals are modified compared to the reference sequence SEQ ID NO:1 by deletion, insertion, substitution or a combination thereof and that still has at least 10%, 50%, 80%, in particular more than 92% of the enzymatic activity of the enzyme having the reference sequence SEQ ID NO:1, wherein enzymatic activity for an enzyme alkB-type oxidoreductase may be understood as meaning the ability preferably to convert butane to 1-butanol and/or 2-butanol when butane is used as the carbon source, that is when butane is used as the $C_4$ molecule according to any aspect of the present invention.

The oxidoreductase may be a monooxygenase. In particular, the monooxygenase may be a P450 type monooxygenase, e.g. cytochrome P450 from *Candida tropicalis* or from *Cicer arietinum*. More in particular, a CYP153 monooxygenase, e.g. cytochrome P450-monooxygenase from *Alcanivorax borkumensis* SK2 (YP_691921). The monooxygenase may be used in the first oxidation of butane to the alcohol.

In another example, the oxidoreductase may be an NAD(P)H dependent alcohol dehydrogenase (ADH). In particular, the ADH may be from *Escherichia coli* MS 187-1 (ZP_07145023), from *Bacillus stearothermophilus* (P42328), from *Ralstonia eutropha* (ACB78191.1), from *Lactobacillus brevis* (YP_795183.1), from *Lactobacillus kefiri* (ACF95832.1), from horse liver, from *Paracoccus pantotrophus* (ACB78182.1) or from *Sphingobium yanoikuyae* (EU427523.1). In one example, the ADH may be a flavin-dependent ADH, e.g. from *Candida tropicalis* (AAS46878.1). The ADH may be used when butanol is used as the carbon source, that is when butanol is used as the $C_4$ molecule according to any aspect of the present invention, directly or in situ produced from butane.

In one example, the oxidoreductase may be from the glucose-methanol-choline-oxidoreductase family, especially from *Caulobacter* sp. K31 (ABZ74557.1). This particular oxidoreductase may also be used when butanol is used as the carbon source, that is when butanol is used as the $C_4$ molecule according to any aspect of the present invention, directly or in situ produced from butane.

The term "increased activity of an enzyme" is understood as meaning increased intracellular activity.

The description and definitions below in relation to increasing the enzyme activity in cells apply both for the increase in the activity of the enzymes $E_1$ to $E_3$ and oxidoreductase as well as for all subsequently mentioned enzymes in this disclosure, the activity of which can optionally be increased. In particular, all the methods as described throughout this specification in relation to enzymes $E_1$, $E_2$ and $E_3$ may apply to the enzyme oxidoreductase that may be optionally present in the recombinant cell according to any aspect of the present invention.

In principle, an increase in the enzymatic activity can be achieved by increasing the copy number of the gene sequence or the gene sequences which code for the enzyme, using a strong promoter or an improved ribosome binding site, attenuating a negative regulation of gene expression, for example by transcription regulators, or amplifying a positive regulation of gene expression, modifying the codon usage of the gene, in various ways increasing the half-life of the mRNA or of the enzyme, modifying the regulation of the expression of the gene or utilizing a gene or allele that codes for an appropriate enzyme having an increased activity and optionally combining these measures. According to any aspect of the present invention, genetically modified cells are produced, for example, by transformation, transduction, conjugation or a combination of these methods using a vector that contains the desired gene, an allele of this gene or parts thereof and optionally contains a promoter making possible the expression of the gene. Heterologous expression is in particular achieved by integration of the gene or the alleles in the chromosome of the cell or an extrachromosomally replicating vector.

DE-A-10031999 gives several examples of ways to increase the enzyme activity in cells as exemplified by pyruvate carboxylase. A skilled person would easily be able to use the methods disclosed in DE-A-10031999 for increasing the enzyme activity in the cells according to any aspect of the present invention.

The expression of the above and all subsequently mentioned enzymes or genes is detectable with the aid of 1- and/or 2-dimensional protein gel separation and subsequent optical identification of the protein concentration in the gel using appropriate analytical software. If the increase in an enzyme activity is based exclusively on an increase in the expression of the corresponding gene, the quantification of the increase in the enzyme activity can be determined in a simple manner by a comparison of the 1- or 2-dimensional protein separations between wild-type and genetically modified cell. A customary method for the preparation of the protein gels in the case of *corynebacterium* and for the identification of the proteins is the procedure described by Hermann et al., 2001. The protein concentration may be analyzed by Western Blot hybridization using an antibody specific for the protein to be detected (Sambrook et al., 1989) and subsequent optical analysis using appropriate software for the concentration determination (Lohaus and Meyer, 1989). The activity of DNA-binding proteins can be measured by means of DNA band shift assays (also called gel retardation) (Wilson et al., 2001). The action of DNA-binding proteins on the expression of other genes can be detected by various well-known methods of the reporter gene assay (Sambrook et al., 1989). The intracellular enzymatic activities can also be determined according to various established methods (Donahue at al., 2000; Ray at al., 2000; Freedberg at al., 1973). If in the following examples no specific methods are indicated for the determination of the activity of a precise enzyme, the determination of the increase in the enzyme activity or the determination of the decrease of an enzyme activity may take place by means of methods described in Hermann et al., 2001, Lohaus at al., 1998, Lottspeich, 1999 and Wilson at al., 2001.

If the increase in the enzyme activity is accomplished by mutation of the endogenous gene, such mutations can be randomly produced either by conventional methods, such as, for example, by UV Irradiation or by mutagenic chemicals, or selectively by means of genetic engineering methods such as deletion(s), insertion(s) and/or nucleotide exchange(s). Modified cells are obtained by these mutations. Mutants of enzymes are in particular also those enzymes that are no longer feedback-, product- or substrate-inhibitable or are so to a reduced degree at least in comparison to the wild-type enzyme.

If the increase in the enzyme activity is accomplished by increase in the synthesis of an enzyme, the copy number of the corresponding genes may be increased or the promoter and regulation region or the ribosome binding site, which is situated upstream of the structural gene, may be mutated. Expression cassettes, which are incorporated upstream of the structural gene, act in the same manner. It is also possible, by means of at least inducible promoters, to increase the expression the gene at any desired point in time. "Enhancers" may also be assigned to the enzyme gene of interest as regulatory sequences, which likewise bring about increased gene expression by means of an improved interaction between RNA polymerase and DNA. As a result of measures for the prolongation of the lifetime of the mRNA, the expression is likewise improved. Also, by prevention of the degradation of the enzyme protein the enzyme activity may also be increased. The genes or gene constructs are present here either in plasmids having a different copy number or are integrated and amplified in the chromosome. In another example, an overexpression of the genes concerned can be achieved by modification of the media composition and culture management. A person skilled in the art finds directions for this, inter alia, in Martin et al., 1987, Guerrero et al., 1994, Tsuchlya and Morinaga, 1988, Eikmanns et al., 1991, EP-A-0472869, U.S. Pat. No. 4,601,893, Schwarzer and Pühler, 1991, Reinscheld et al., 1994, LaBarre et al., 1993, WO96/15246A, Malumbres et al., 1993, JP10229891A, Jensen and Hammer, 1998 and in known textbooks of genetics and molecular biology. The measures described above likewise result in, like the mutations, to genetically modified cells that may be used in any aspect of the present invention.

Episomal plasmids, for example, are employed for increasing the expression of the respective genes. Suitable plasmids or vectors are in principle all theoretically available for this purpose to the person skilled in the art. Such plasmids and vectors can be taken, for example, from the brochures of companies Novagen, Promega, New England Biolabs, Clontech or Gibco BRL. In particular, plasmids and vectors can be found in: Glover, D. M., 1985, Rodriguez, R. L. and Denhardt, D. T, 1988, Butterworth, Stoneham; Goeddel, D. V., 1990, Fritsch, E. F. and Maniatis, T., 1989.

The plasmid vector, which comprises the gene to be amplified, is then converted to the desired strain by conjugation or transformation. The method of conjugation is described, for example, in Schäfer et al., 1994. Methods for transformation are described, for example at least in Thierbach et al., 1988, Dunican and Shivnan, 1989 and Tauch et al., 1994. After homologous recombination by means of a "cross-over" event, the resulting strain comprises at least two copies of the gene concerned. Using this method at least the copy number of the genes may be increased to a desired number in the strain.

Under the formulation used above and in the following examples "an activity of an enzyme ($E_x$) increased in comparison to its wild-type" is always to be understood as meaning an activity of the respective enzyme $E_x$ increased by a factor of at least 2, particularly of at least 10, more particularly of at least 100, even more particularly of at least 1,000 and most particularly of at least 10,000. The cell according to any aspect of the present invention, which has "an increased activity of an enzyme ($E_x$) compared to its wild-type", in particular also comprises a cell, whose wild-type contains no or at least no detectable activity of this enzyme $E_x$ and which shows a detectable activity of this enzyme $E_x$ only after increasing the enzyme activity, for example by overexpression. In this connection, the term "overexpression" or the formulation used in the following examples "increasing the expression" also comprises the case where a starting cell, for example a wild-type cell, has no or at least no detectable expression and a detectable synthesis of the enzyme $E_x$ is induced only by recombinant methods. $E_x$ may also refer to oxidoreductase.

"Wild-type" of a cell herein designates a cell, the genome of which is present in a state as is formed naturally by evolution. The term is used both for the entire cell as well as for individual genes. The term "wild-type" therefore in particular does not include those cells or those genes, the gene sequences of which have been modified at least partially by man by means of recombinant methods.

In particular, the increase in enzyme activity relative to the wild type cell may be measured using conventional methods known in the art. For example, the increase in activity of $E_1$, $E_2$ and $E_3$ may be measured using the methods disclosed in Burger, M. M., 1963 and Burger, M. M., 1966.

Changes of amino acid radicals of a given polypeptide sequence, which lead to no significant changes in the properties and function of the given polypeptide, are known to the person skilled in the art. Thus, for example, "conserved amino acids" can be mutually exchanged. Examples of such suitable amino acid substitutions include but are not limited to: Ala for Ser; Arg for Lys; Asn for Gin or His; Asp for Glu; Cys for Ser; Gin for Asn; Glu for Asp; Gly for Pro; His for Asn or Gin; lie for Leu or Val; Leu for Met or Val; Lys for Arg or Gin or Glu; Met for Leu or lie; Phe for Met or Leu or Tyr; Ser for Thr; Thr for Ser; Trp for Tyr; Tyr for Trp or Phe; Val for lie or Leu. It is likewise known that changes, particularly at the N- or C-terminus of a polypeptide, in the form of, for example, amino acid insertions or deletions often exert no significant influence on the function of the polypeptide.

The activity of an enzyme can be determined by disrupting cells which contain this activity in a manner known to the person skilled in the art, for example with the aid of a ball mill, a French press or an ultrasonic disintegrator. Subsequently, the separation of cells, cell debris and disruption aids, such as, for example, glass beads, may be carried out by at least centrifugation for 10 minutes at 13,000 rpm and 4° C.

Using the resulting cell-free crude extract, enzyme assays with subsequent LC-ESI-MS detection of the products can then be carded out. Alternatively, the desired enzyme can be enriched by a means known to the person skilled in the art for example by chromatographic methods (such as nickel-nitrilotriacetic acid affinity chromatography, streptavidin affinity chromatography, gel filtration chromatography or ion-exchange chromatography) or else purified to homogeneity.

The activity of the enzyme $E_1$ may be determined using the enzyme samples obtained as described above in the following way: A standard assay may contain 100 µM $E.$ $coli$ ACP, 1 mM i-mercaptoethanol, 200 µM malonyl-coenzyme A, 40 µM octanoyl-coenzyme A (for $E_{1a}$) or dodecanoyl-coenzyme A (for $E_{1b}$), 100 µM NADPH, 2 µg of $E.$ $coli$ FabD, 2 µg of $Mycobacterium$ $tuberculosis$ FabH, 1 µg of $E.$ $coli$ FabG, 0.1 M sodium phosphate buffer, pH 7.0, and 5 µg of enzyme $E_1$ in a final volume of 120 µL. ACP, β-mercaptoethanol and sodium phosphate buffer are incubated for 30 min at 37° C. to reduce the ACP completely. The reaction may then be started by addition of enzyme $E_1$. The reactions may be stopped using 2 ml of water, which has been acidified with HCl to pH 2.0, and subsequently extracted twice with 2 ml of chloroform/methanol (2:1 (v:v)). Phase separation is then carried out by centrifugation (16,100 g, 5 min, RT). The lower organic phase may be removed, evaporated completely in the vacuum centrifuge and the sediment may be taken up in 50 µl of methanol. Undissolved constituents are removed as sediments by centrifugation (16,100 g, 5 min, RT) and the sample is analyzed by means of LC-ESI-MS. The identification of the products takes place by analysis of the corresponding mass traces and the $MS^2$ spectra.

The activity of the enzyme $E_2$ may be determined as follows using the enzyme samples obtained as described above in the following way: A standard assay may contain 185 µl of 10 mM tris-HCl (pH 7.5), 10 µl of 125 mM dTDP-rhamnose and 50 µl of protein crude extract (about 1 mg of total protein) or purified protein in solution (5 µg of purified protein). The reaction is started by the addition of 10 µl of 10 mM ethanolic solution of 3-hydroxydecanoyl-3-hydroxydecanoic acid (for $E_{2a}$) or 3-hydroxy-tetradecanoyl-3-hydroxytetradecanoic acid (for $E_{2b}$) and incubated for 1 h at 30° C. with shaking (600 rpm). Subsequently, the reaction may be treated with 1 ml of acetone. Undissolved constituents are removed as sediments by centrifugation (16,100 g, 5 min, RT) and the sample is analyzed by means of LC-ESI-MS. The identification of the products takes place by analysis of the corresponding mass traces and the $MS^2$ spectra.

The activity of the enzyme $E_3$ may be determined as follows using the enzyme samples obtained as described above: A standard assay may contain 185 µl of 10 mM tris-HCl (pH 7.5), 10 µl of 125 mM of dTDP-rhamnose and 50 µl of protein crude extract (about 1 mg of total protein) or purified protein in solution (5 µg of purified protein). The reaction is started by the addition of 10 µl of 10 mM ethanolic solution of a-L-rhamnopyranosyl-3-hydroxydecanoyl-3-hydroxydecanoic acid (for $E_{3a}$) or a-L-rhamnopyranosyl-3-hydroxytetradecanoyl-3-hydroxytetradecanoic acid (for $E_{3b}$) and incubated for 1 h at 30° C. with shaking (600 rpm). Subsequently, the reaction is treated with 1 ml of acetone. Undissolved constituents are sedimented by centrifugation (16,100 g, 5 min, RT) and the sample is analyzed by means of LC-ESI-MS. The identification of the products takes place by analysis of the corresponding mass traces and the $MS^2$ spectra.

The recombinant cells according to any aspect of the present invention may have increased activities of at least $E_1$, $E_2$ and/or $E_3$. In particular, the cells may have increased activity of $E_1$, $E_2$ or $E_3$ or combinations thereof. More in particular, the cells may have increased activity of $E_1$, $E_2$ and $E_3$. In one example, the cells have increased activity of $E_1$ and $E_2$, or $E_1$ and $E_3$, or $E_2$ and $E_3$.

The activity of the enzyme oxidoreductase may be determined by any method known in the art. In particular, the activity of alkB-type oxidoreductase may be determined using the method disclosed in WO2009/077461A1, the activity of P450 type monooxygenases may be determined using the method provided in Scheps, D et al., 2011 and the activity of ADH by the method provided in Benson, S., Shapiro, J., J. Bacteriol. 1976, 126, 794-798.

The genetically modified cells according to any aspect of the present invention can be brought into contact with the medium continuously or discontinuously in the batch process (batch culture) or in the fed-batch process (feed process) or repeated fed-batch process (repetitive feed process) for the purpose of the production of the abovementioned products and thus cultured. A semi-continuous process is also conceivable, as is described in GB-A-1009370. A summary of known culturing methods is described in the textbook of Chmiel or in the textbook of Storhas. The culture medium to be used must satisfy in a suitable manner the demands of the respective strains. Descriptions of culture media of different yeast strains are contained, for example, in Klaus Wolf, 1996.

The cells according to any aspect of the present invention can be prokaryotes or eukaryotes. These can be mammalian cells (such as, for example, cells from man), plant cells or microorganisms such as yeasts, fungi or bacteria, wherein microorganisms are particularly preferred and bacteria and yeasts are most preferred.

Suitable bacteria, yeasts or fungi are in particular those bacteria, yeasts or fungi that are deposited in the Deutsche Sammlung von Mikroorganismen und Zellkulturen (German Collection of Microorganisms and Cell Cultures) GmbH (DSMZ), Brunswick, Germany, as bacterial, yeast or fungal strains. Bacteria suitable according to the invention belong to the genera that are listed under:

http://www.dsmz.de/species/bacteria.htm, yeasts suitable according to the invention belong to those genera that are listed under:

http://www.dsmz.de/species/yeasts.htm and fungi suitable according to the invention are those that are listed under.

http://www.dsmz.de/species/fungi.htm.

In particular, the cells may be selected from the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillium, Rhodobacter, Burkholderia, Clostridium* and *Cupriavidus*. More in particular, the cells may be selected from the group consisting of *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. caledonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronellolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, 'P. blatchfordae', P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. ficuserectae, 'P. helianthi', P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides, Saccharomyces cerevisiae, Yarrowia lipolytica* and *Zymomonas mobile*. Even more in particular, the cells may be selected from the group consisting of *Pseudomonas putida, Escherichia coli* and *Burkholderia thailandensis*.

According to any aspect of the present invention, the cells in their wild-type may be incapable of forming detectable amounts of rhamnolipids and/or have none or no detectable activity of the enzymes $E_1$, $E_2$. $E_3$ and/or oxidoreductase.

It is advantageous according to any aspect of the present invention that the cell be able in its wild type to from polyhydroxyalkanoates having chain lengths of the monoalkanoate of $C_6$ to $C_{16}$. Such cells are, for example, *Burkholderia* sp., *Burkholderia thailandensis, Pseudomonas* sp., *Pseudomonas putida, Pseudomonas aeruginosa, Pseudomonas oleovorans, Pseudomonas stutzeri, Pseudomonas fluorescens, Pseudomonas citronellolis, Pseudomonas resinovorans, Comamonas testosteroni, Aermonas hydrophila, Cupriavidus necator, Alcaligenes latus* and *Ralstonia eutropha*. In this connection, cells according to any aspect of the present invention may be genetically modified such that, compared to their wild-type, they are able to form fewer polyhydroxyalkanoates. Such cells are described, for example, at least in De Eugenio et al., 2010, and Rehm et al., 2001. Such a recombinant cell, able to form fewer polyhydroxyalkanoates compared to its wild-type, is in particular characterized in that, compared to its wild-type, it has a decreased activity of at least one enzyme $E_3$ or $E_{10}$.

$E_9$ represents a polyhydroxyalkanoate synthase, EC:2.3.1., in particular having polypeptide sequence SEQ ID NO:20 ($E_{9a}$) or SEQ ID NO:21 ($E_{9b}$) or having a polypeptide sequence in which up to 25%, 20%, 15% in particular up to 10, 9, 8, 7, 6, 5, 4, 3, 2, 1% of the amino acid radicals compared to the respective reference sequence SEQ ID NO:20 or SEQ ID NO:21 are modified by deletion, insertion, substitution or a combination thereof and that still has at least 10%, 50%, particularly 80%, in particular more than 90% of the enzymatic activity of the enzyme having the respective reference sequence SEQ ID NO:20 or SEQ ID NO:21, wherein enzymatic activity for an enzyme $E_9$ ($E_{9a}$ and $E_{9b}$) may be understood as meaning the ability to convert 3-hydroxyalkanoyl-coenzyme A to poly-3-hydroxyalkanoic acid, in particular 3-hydroxytetradecanoyl-coenzyme A to poly-3-hydroxytetradecanoic acid.

$E_{10}$ represents a 3-hydroxyalkanoyl-ACP:coenzyme A transferase, in particular having polypeptide sequence SEQ ID NO:22 ($E_{10a}$) or SEQ ID NO:23 ($E_{10b}$) or having a polypeptide sequence in which up to 25%, 20%, particularly 15% in particular up to 10, 9, 8, 7, 6, 5, 4, 3, 2, 1% of the amino acid radicals are modified compared to the respective reference sequence SEQ ID NO:22 or SEQ ID NO:23 by deletion, insertion, substitution or a combination thereof and that still has at least 10%, 50%, particularly 80%, in particular more than 90% of the enzymatic activity of the enzyme having the respective reference sequence SEQ ID NO:22 ($E_{10a}$) or SEQ ID NO:23 ($E_{10b}$), wherein enzymatic activity for an enzyme $E_{10}$ ($E_{10a}$ and $E_{10b}$) may be understood as meaning the ability to convert 3-hydroxyalkanoyl-ACP 20 to 3-hydroxy-alkananoyl-coenzyme A, in particular 3-hydroxyalkananoyl-ACP to 3-hydroxytetradecanoyl-coenzyme A.

The activity of the enzyme $E_9$ ($E_{9a}$ and $E_{9b}$) may be determined for example by using the samples obtained as described above for the enzymes $E_1$ to $E_3$, by first mixing 560 μl of 100 mM tris/HCl, pH 7.5, 20 μl of 35 mM DTNB in DMSO and 20 μl of 41 mM 3-hydroxydecanoyl-coenzyme A. Subsequently, 5 μg of purified enzyme $E_9$ in 100 μl of tris/HCl, pH 7.5 are added, and subsequently the increase in the extinction at 412 nm (caused by addition of 5,5'-dithiobis(2-nitrobenzoate) (DTNB) to free SH groups) over time (ΔE/min) is recorded continuously for 1 min in a spectrophotometer.

The activity of the enzyme $E_{10}$ ($E_{10a}$ and $E_{10b}$) may be determined for example by using the samples obtained as described above for the enzymes $E_1$ to $E_3$. The standard assay may contain 3 mm $MgCl_2$, 40 μm hydroxydecanoyl-coenzyme A and 20 μm E. coli ACP In 50 mm tris-HCl, pH 7.5, in a total volume of 200 μl. The reaction is started by addition of 5 μg of purified enzyme $E_{10}$ in 50 μl of tris/HCl, pH 7.5 and incubated for 1 h at 30° C. The reaction is stopped by addition of 50% (w/v) trichloroacetic acid and 10 mg/ml ml of BSA (30 μl). The released coenzyme A may be determined spectrophotometrically by recording the increase in the extinction at 412 nm, caused by addition of 5,5'-dithiobis(2-nitrobenzoate) (DTNB) to free SH groups, over time.

The phrase "decreased activity of an enzyme $E_x$" used with reference to any aspect of the present invention may be understood as meaning an activity decreased by a factor of at least 0.5, particularly of at least 0.1, more particularly of at least 0.01, even more particularly of at least 0.001 and most particularly of at least 0.0001. The phrase "decreased activity" also comprises no detectable activity ("activity of zero"). The decrease in the activity of a certain enzyme can be effected, for example, by selective mutation or by other measures known to the person skilled in the art for decreasing the activity of a certain enzyme.

In particular, the person skilled in the art finds instructions for the modification and decrease of protein expression and concomitant lowering of enzyme activity especially for Pseudomonas and Burkholderia, by means of interrupting specific genes, for example at least in Dubeau et al. 2009., Singh & Röhm. 2008., Lee et al., 2009 and the like.

Cells according to any aspect of the present invention are characterized in that the decrease in the enzymatic activity is achieved by modification of a gene comprising one of the nucleic acid sequences, wherein the modification is selected from the group comprising, consisting of, insertion of foreign DNA In the gene, deletion of at least parts of the gene, point mutations in the gene sequence, RNA Interference (siRNA), antisense RNA or modification (insertion, deletion or point mutations) of regulatory sequences, such as, for example, promoters and terminators or of ribosome binding sites, which flank the gene.

Foreign DNA is to be understood in this connection as meaning any DNA sequence which is "foreign" to the gene (and not to the organism), i.e. endogenous DNA sequences can also function in this connection as "foreign DNA". In this connection, it is particularly preferred that the gene is interrupted by insertion of a selection marker gene, thus the foreign DNA is a selection marker gene, wherein preferably the insertion was effected by homologous recombination in the gene locus.

In particular, the cells that may be used according to any aspect of the present invention may be Pseudomonas putida cells, which have a decreased polyhydroxyalkanoate synthesis compared to their wild-type. Such cells are described, for example, at least as KTOY01 and KTOY02 in Ren et al., 1998, Huisman et al., 1991, De Eugenio et al., 2010 and Ouyang et al. 2007.

The rhamnolipids formed according to the method of the present invention may at least be of the general formula (I) or its salt,

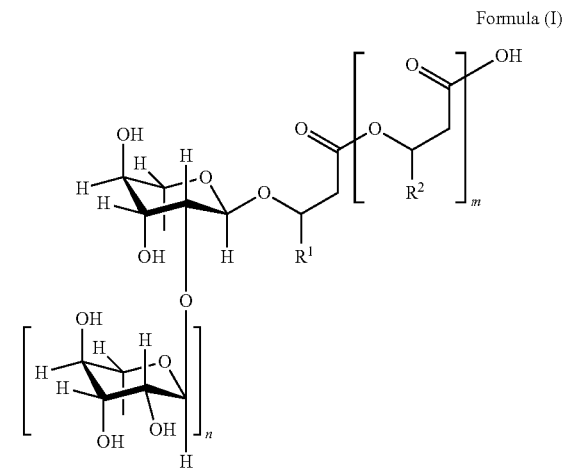

Formula (I)

wherein
m=2, 1 or 0, in particular 1 or 0,
n=1 or 0, in particular 1,
$R^1$ and $R^2$=independently of one another identical or different organic radical having 2 to 24, preferably 5 to 13 carbon atoms, in particular optionally branched, optionally substituted, in particular hydroxy-substituted, optionally unsaturated, in particular optionally mono-, di- or tri-unsaturated, alkyl radical, that may be selected from the group consisting of pentenyl, heptenyl, nonenyl, undecenyl and tridecenyl and $(CH_2)_o$—$CH_3$ with o=1 to 23, preferably 4 to 12.

For the case where the cell according to any aspect of the invention is able to form a rhamnolipid having m=1, the radical may be

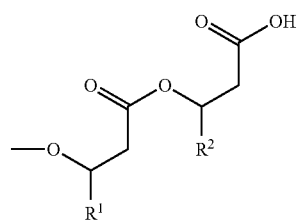

defined by means of R¹ and R² is derived from 3-hydroxyoctanoyl-3-hydroxyoctanoic acid, 3-hydroxyoctanoyl-3-hydroxydecanoic acid, 3-hydroxydecanoyl-3-hydroxyoctanoic acid, 3-hydroxyoctanoyl-3-hydroxydecenoic acid, 3-hydroxydecenoyl-3-hydroxyoctanoic acid, 3-hydroxyoctanoyl-3-hydroxydodecanoic acid, 3-hydroxydodecanoyl-3-hydroxyoctanoic acid, 3-hydroxyoctanoyl-3-hydroxydodecenoic acid, 3-hydroxydodecanoyl-3-hydroxyoctanoic acid, 3-hydroxydecanoyl-3-hydroxydecanoic acid, 3-hydroxydecenoyl-3-hydroxydecanoic acid, 3-hydroxydecanoyl-3-hydroxydecenoic acid, 3-hydroxydecanoyl-3-hydroxydecanoic acid, 3-hydroxydecenoyl-3-hydroxydecenoic acid, 3-hydroxydecanoyl-3-hydroxydodecanoic acid, 3-hydroxydodecanoyl-3-hydroxydecanoic acid, 3-hydroxydecanoyl-3-hydroxydodecenoic acid, 3-hydroxydodecenoyl-3-hydroxydecanoic acid, 3-hydroxydecanoyl-3-hydroxytetradecenoic acid, 3-hydroxytetradecanoyl-3-hydroxydecenoic acid, 3-hydroxydodecenoyl-3-hydroxydecanoic acid, 3-hydroxydecanoyl-3-hydroxytetradecanoic acid, 3-hydroxytetradecanoyl-3-hydroxydecanoic acid, 3-hydroxydecanoyl-3-hydroxytetradecenoic acid, 3-hydroxytetradecenoyl-3-hydroxydecanoic acid, 3-hydroxydodecanoyl-3-hydroxydodecanoic acid, 3-hydroxydodecanoyl-3-hydroxydodecanoic acid, 3-hydroxydodecanoyl-3-hydroxydodecenoic acid, 3-hydroxydodecenoyl-3-hydroxydodecanoic acid, 3-hydroxytetradecanoyl-3-hydroxytetradecanoic acid, 3-hydroxydodecanoyl-3-hydroxytetradecanoyl-3-hydroxytetradecanoic acid, 3-hydroxyhexedecanoyl-3-hydroxytetradecanoic acid, 3-hydroxytetradecanoyl-3-hydroxyhexadecanoic acid or 3-hydroxyhexadecanoyl-3-hydroxyhexadecanoic acid.

It is obvious to the person skilled in the art that according to any aspect of the present invention, mixtures of different rhamnolipids of the general formula (I) may be formed.

In this connection, the cells according to any aspect of the present invention may be able to form mixtures of rhamnolipids of the general formula (I), which are characterized in that in more than 80% by weight, more than 90% by weight, particularly more than 95% by weight of the rhamnolipids formed n is =1 and the radical defined by means of R¹ and R² is derived in less than 10% by weight, less than 5% by weight, particularly less than 2% by weight of the rhamnolipids formed, from 3-hydroxydecanoyl-3-hydroxyoctanoic acid or 3-hydroxyoctanoyl-3-hydroxydecanoic acid, wherein the % by weight indicated refers to the sum of all rhamnolipids of the general formula (I) formed.

Since the cells according to any aspect of the present invention can be used advantageously for the production of rhamnolipids and since these lipids are subsequently optionally purified, it is advantageous if the cells according to any aspect of the present invention have an increased activity compared to their wild-type of at least an enzyme $E_8$, which catalyzes the export of a rhamnolipid of the general formula (I) from the cell into the surrounding medium.

In this connection proteins $E_8$ are selected from the group consisting of an enzyme $E_8$ having polypeptide sequence SEQ ID NO:16 ($E_{8a}$), SEQ ID NO:17 ($E_{8b}$), SEQ ID NO:18 ($E_{8c}$) or SEQ ID NO:19 ($E_{8d}$) or having a polypeptide sequence in which up to 25%, up to 20%, particularly up to 15% in particular up to 10, 9, 8, 7, 6, 5, 4, 3, 2, 1% the amino acid radicals are modified by deletion, insertion, substitution or a combination thereof compared to the respective reference sequence SEQ ID NO:16 ($E_{8a}$), SEQ ID NO:17 ($E_{8b}$), SEQ ID NO:18 ($E_{8c}$) or SEQ ID NO:19 ($E_{8d}$) and that still has at least 50%, 65%, particularly 80%, in particular more than 90% of the enzymatic activity of the enzyme having the respective reference sequence SEQ ID NO:16 ($E_{8a}$), SEQ ID NO:17 ($E_{8b}$), SEQ ID NO:185 ($E_{8c}$) or SEQ ID NO:19 ($E_{8d}$), wherein enzymatic activity for an enzyme $E_8$ ($E_{8a}$, $E_{8b}$ $E_{8c}$ and $E_{8d}$), is understood as meaning the ability to export a rhamnolipid of the general formula (I) from the cell into the surrounding medium.

TABLE 1

Sequences of the enzymes used according to any aspect of the present invention.

| SEQ ID NO | SEQUENCE |
|---|---|
| 1 | EKHRVLDSAPEYVDKKKYLWILSTLWPATPMIGIWLANETGWGIFYGLVLLVWYGALP LLDAMFGEDFNNPPEEVVPKLEKERYYRVLTYLTVPMHYAALIVSAWWVGTQPMSWLEIG ALALSLGIVNGLALNTGHELGHKKETFDRWMAKIVLAVVGYGHFFIEHNKGHHRDVATPM DPATSRMGESIYKFSIREIPGAFIRAWGLEEQRLSRRGQSVWSFDNEILQPMIITVILYA VLLALFGPKMLVFLPIQMAFGWWQLTSANYIEHYGLLRQKMEDGRYEHQKPHHSWNSNHI VSNLVLFHLQRHSDHHAHPTRSYQSLRDFPGLPALPTGYPGAFLMAMIPQWFRSVMDPKV VDWAGGDLNKIQIDDSMRETYLKKFGTSSAGHSSSTSAVAS |
| 2 | MRRESLLVSVCKGLRVHVERVGQDPGRSTVMLVNGAMATTASFARTCKCLAEHFNVVLFD LPFAGQSRQHNPQRGLITKDDEVEILLALIERFEVNHLVSASWGGISTLLALSRNPRGIR SSVVMAFAPGLNQAMLDYVGRAQALIELDDKSAIGHLLNETVGKYLPPRLKASNHQHMAS LATGEYEQARFHIDQVLALNDRGYLACLERIQSHVHFINGSWDEYTTAEDARQFRDYLPH CSFSRVEGTGHFLDLESKLAAVRVHRALLEHLLKQPEPQRAERAAGFHEMAIGYA |
| 3 | MRGSGEWVAAAARVRQGGQIAREGGYVEASIKGAGSAHLPSRCGRYAMPIEKQVVALPSG LKVHVERHVFDPAFETVILVNGALATTASFGQTIRYLGERVNAVCFDLPYAGQSRQHNPG EYILTKDDEVEILLHLAERFEPSFLLSVSWGGVASLFALARGCASVRRAVIASFSPFLND AMTDYVTRARDHIAAGENLKAAQLLNDTVGRYLPRIMKLYNYRYLTKLPRTEQDQVAFHV DQILSMRPEQYLPEFRQIGCAVKFINGELDEYTTASDVRRLAAYVRRAEFATIRQAGHFL DLEGRQQQEQLRAAILGFFGDERASAARDDAQDETLAPLGQLPALS |
| 4 | MRRESLLVSVCKGLRVHVERVGQDPGRSTVMLVNGAMATTASFARTCKCLAEHFNVVLFD LPFAGQSRQHNPQRGLITKDDEVEILLALIERFEVNHLVSASWGGISTLLALSRNPRGIR SSVVMAFAPGLNQAMLDYVGRAQALIELDDKSAIGHLLNETVGKYLPPRLKASNHQHMAS LATGEYEQARFHIDQVLALNDRGYLACLERIQSHVHFINGSWDEYTTAEDARQFRDYLPH CSFSRVEGTGHFLDLESKLAAVRVHRALLEHLLKQPEPQRAERAAGFHEMAIGYA |

TABLE 1-continued

Sequences of the enzymes used according to any aspect of the present invention.

| SEQ ID NO | SEQUENCE |
|---|---|
| 5 | MRRESLLVSVCKGLRVHVERVGQDPGRSTVMLVNGAMATTASFARTCKCLAEHFNVVLFD<br>LPFAGQSRQHNPQRGLITKDDEVEILLALIERFEVNHLVSASWGGISTLLALSRNPRGIR<br>SSVVMAFAPGLNQAMLDYVGRAQALIELDDKSAIGHLLNETVGKYLPQRLKASNHQHMAS<br>LATGEYEQARFHIDQVLALNDRGYLACLERIQSHVHFINGSWDEYTTAEDARQFRDYLPH<br>CSFSRVEGTGHFLDLESKLAAVRVHRALLEHLLKQPEPQRAERAAGFHEMAIGYA |
| 6 | MRRESLLVTVCKGLRVHVERVGQDPGRDTVMLVNGAMATTASFARTCKCLAEHFNVVLFD<br>LPFAGQSRQHNPQRGLITKDDEVEILLALIERFAVNHLVSASWGGISTLLALSRNPRGVR<br>SSVVMAFAPGLNQAMLDYVGRAQELIELDDKSAIGHLLNETVGKYLPPRLKASNHQHMAS<br>LATGEYEQARFHIDQVLALNDRGYLSCLGQIQSHVHFINGSWDEYTTAEDARQFRDYLPH<br>CSFSRVEGTGHFLDLESKLAAARVHRALLEHLLAQPEPWRSEQAAGFHEMAIGYA |
| 7 | MHAILIAIGSAGDVFPFIGLARTLKLRGHRVSLCTIPVFRDAVEQHGIAFVPLSDELTYR<br>RTMGDPRLWDPKTSFGVLWQTIAGMIEPVYEYVSAQRHDDIVVVGSLWALGARIAHEKYG<br>IPYLSAQVSPSTLLSAHLPPVHPKFNVPEQMPLAMRKLLWRCIERFKLDRTCAPDINAVR<br>RKVGLETPVKRIFTQWMHSPQGVVCLFPAWFAPPQQDWPQLHMTGFPLFDGSIPGTPLD<br>DELQRFLDQGSRPLVFTQGSTEHLQGDFYAMALRALERLGARGIFLTGAGQEPLRGLPNH<br>VLQRAYAPLGALLPSCAGLVHPGGIGAMSLALAAGVPQVLLPCAHDQFDNAERLVRLGCG<br>MRLGVPLREQELRGALWRLLEDPAMAAACRRFMELSQPHSIACGKAAQVVERCHREGDAR<br>WLKAAS |
| 8 | MDAGRIGLHDAAAAGRIGMTEAFASRARCSAAALAAGGRAPAGDGRSGSNRAAANGSVDC<br>RAGWNDEAMAKVIVTAIGSAGDVHPLLGVSRALSARGHEVVFCTHAPFEAAVRASGFAFV<br>PVGTAEDYVRAMADPALWDPRTSFKTLWRVIAPVVRPHFEVLRALSDADTVLVGTLWAFS<br>ARLMQERFGTRYVSVQVSPSTLLSAHAPPTHKRLTIPKGLPLAVKAGLMTLIERQVLDRV<br>CGPELNAARQALGLAPAKRILGRWLHSTDGVLCLFPSWFAPAQPDWPANHLQSGFPLFND<br>AGPAQADAELEAFVASGEAPVVFTAGSTLVDGRTYEHAVTQVLQATGVRGILLAPDAPDA<br>PAASDGAALLKRRYVPLAALLPRCRALVHHGGIGTASLAYAAGVPQVVTPFAHDQFDNAQ<br>RVAASGCGVRLDAPVRGEPLARALAQVLGDAAMAARCAQVRARMAAEPNGCDAAARFIER<br>FAPGVAARRAQPA |
| 9 | MHAILIAIGSAGDVFPFIGLARTLKLRGHRVSLCTIPVFRAAVEQHGIEFVPLSDELTYR<br>RTMGDPRLWDPKTSFGVLWQAIAGMIEPVYEYVCAQRHDDIVVVGSLWALGARIAHEKYG<br>IPYLSVQVSPSTLLSAHLPPVHPRFNVPEQVPLAMRKLLWRCIERFKLDRTCAPEINAVR<br>RKVGLVGPAKRIFTQWMHSPQGVLCLFPAWFAPPQQDWPQLHMTGFPLFDGSVPGTRLD<br>DELQRFLEQGSRPLVFTQGSTEHLQGDFYAMALRALERLGARGIFLTGAGQEPLRGLPSH<br>VLQRSYVPLGALLPACAGLVHPAGIGAMSLALAAGVPQVLLPCAHDQFDNAERLVRLGCG<br>IRLGLPLREQALRESLWRLLEDPALAAACRRFMELSQPHSIACGKAAQVVERCHREGDVR<br>WLKAAS |
| 10 | MHAILIAIGSAGDVFPFIGLARTLKLRGHRVSLCTIPVFRDAVEQHGIAFVPLSDELTYR<br>RTMGDPRLWDPKTSFGVLWQAIAGMIEPVYEYVSAQRHDDIVVVGSLWALGARIAHEKYG<br>IPYLSAQVSPSTLLSAHLPPVHPKFNVPEQMPLAMRKLLWRCIERFKLDRTCAPEINAVR<br>RKVGLETPVKRIFTQWMHSPQGVVCLFPAWFAPPQQDWPQLHMTGFPLFDGSIPGTPLD<br>DELQRFLDQGSRPLVFTQGSTEHLQGDFYAMALRALERLGARGIFLTGAGQEPLRGLPNH<br>VLQRAYAPLGALLPSCAGLVHPGGIGAMSLALAAGVPQVLLPCAHDQFDNAERLVRLGCG<br>MRLGVPLREQELRGALWRLLEDPAMAAACRRFMELSQPHSIACGKAAQVVERCHREGDAR<br>WLKAAS |
| 11 | MHAILIAIGSAGDVFPFIGLARTLKLRGHRVSLCTIPVFRDAVEQHGIAFVPLSDELTYR<br>RTMGDPRLWDPKTSFGVLWQAIAGMIEPVYEYVSAQRHDDIVVVGSLWALGARIAHEKYG<br>IPYLSAQVSPSTLLSAHLPPVHPKFNVPEQMPLAMRKLLWRCIERFKLDRTCAPEINAVR<br>RKVGLETPVKRIFTQWMHSPQGVVCLFPAWFAPPQQDWPQLHMTGFPLFDGSIPGTPLD<br>DELQRFLDQGSRPLVFTQGSTEHLQGDFYAMALRALERLGARGIFLTGAGQEPLRGLPNH<br>VLQRAYAPLGALLPSCAGLVHPGGIGAMSLALAAGVPQVLLPCAHDQFDNAERLVRLGCG<br>MRLGVPLREQELRGALWRLLEDPAMAAACRRFMELSQPHSIACGKAAHVVERCHREGDAR<br>WLKAAS |
| 12 | RIDMGVLVVLFNPGDDDLEHLGELAAAFPQLRFLAVDNSPHSDPQRNARLRGQGIAVL<br>HHGNRQGIAGAFNQGLDALFRRGVQGVLLLDQDSRPGGAFLAAQWRNLQARNGQACLLGP<br>RIFDRGDRRFLPAIHLDGLTLRQLSLDGLTTPQRTSFLISSGCLLTREAYQRLGHFDEEL<br>FIDHVDTEYSLRAQALDVPLYVDPRLVLEHRIGTRKTRRLGGLSLSAMNHAPLRRYYLAR<br>NGLLVLRRYARSSPLALLANLPTLTQGLAVLLLERDKLLKLRCLGWGLWDGLRGRGGALE<br>TNRPRLLKRLAGPAVASVASGKAKA |
| 13 | MTILGALVILYDPTDEQLSGLEALARDSDALVVVDNTPHEHAAARERVRALSARTNTVWR<br>HHGNRGGVAGGYNAGLSVLFAQGVEAVALFDQDSTVPAGYFERMREACAQLGEQPGAHAG<br>AFIAGPRIYDANEQRFLPELMTSGVTVRRVRVEGETAPQRCAFLISSGSVISRAAYARLG<br>RFDEALFIDHVDTEYCLRALAHNVPLYVVPPLVLTHRIGARRRHKVGPFELTAMHHGWLR<br>RYYGARNAMQLGLQYGLRFPVALVPNLLTIWQVIQVVLCEREKGAKLRGIALGVLDGLFG<br>RLGSFDDARAGAAAREPVRQE |
| 14 | MDRIDMGVLVVLFNPGDDDLEHLGELAAAFPQLRFLAVDNSPHSDPQRNARLRGQGIAVL<br>YHGNRQGIAGAFNQGLDTLFRRGLQGVLLLDQDSRPGGAFLAAQWRNLQACNGQACLLGP |

TABLE 1-continued

Sequences of the enzymes used according to any aspect of the present invention.

| SEQ ID NO | SEQUENCE |
|---|---|
| | RIFDRGDRRFLPAIHLDGLALRQLSLDGLTTPQRTSFLISSGCLLTREAYQRLGHFDEEL<br>FIDHVDTEYSLRAQALDVPLYVDPRLVLEHRIGTRKTRRLGGLSLSAMNHAPLRRYYLAR<br>NGLLVLRRYARSSPLALLANLPTLTQGLAVLLLERDKLLKLRCLGWGLWDGLRGRGGALE<br>RNRPRLLKRLAGPAVAPTVPGKAKA |
| 15 | MDRIDMGVLVVLFNPGDDDLEHLGELAAAFPQLRFLAVDNSPHSDPQRNARLRGQGIAVL<br>HHGNRQGIAGAFNQGLDALFRRGVQGVLLLDQDSRPGGAFLAAQWRNLQARNGQACLLGP<br>RIFDRGDRRFLPAIHLDGLTLRQLSLDGLTTPQRTSFLISSGCLLTREAYQRLGHFDEEL<br>FIDHVDTEYSLRAQALDVPLYVDPRLVLEHRIGTRKTRRLGGLSLSAMNHAPLRRYYLAR<br>NGLLVLRRYARSSPLALLANLPTLTQGLAVLLLERDKLLKLRCLGWGLWDGLRGRGGALE<br>RNRPRLLKRLAGPAVASVASGKAKA |
| 16 | VSTTSLCPSATREHGPGAKRVLPLLFLTCLLDAAGVGLIVPLLPTLIGSVAPLAVRDAAT<br>WGAALVMTFALLQLFFSPVLGSISDRFGRRPVLVLAMLGFALSYLLLALADSLWMLFLGR<br>ALAGLTGASVATAMACAADLGTHGQRTRHFGWLYAGLALGMILGPALGGLLAVHGTTLPL<br>LLAAGLCLLNALLAGLFLEETLPPTRRRRLDPRRMNALRSISGLARQPGVGRLLAVLALV<br>FLGLQAVMVVWPFFVIEKFHWSSAWIGYSLALYGVLAVLAQTLGVNLCKRRLDDARLLRL<br>GLALQGCGLLLFALVDSSFWLVCALLPFALGSLATPAMQGLLSARVPVDRQGELQGVLSS<br>LMSLAAIVGPPLMSGLFHWGSGPLAPLPLAGAPFLAGALLVLAGLVLAWQLRPTGEERSW<br>TG |
| 17 | MSADQAGVAPPAAAPLRGAKLALLTFALSLATFIEVLDSTVANVAVPAISGSLGVSNSQG<br>TWVISSYSVAAAIAVPLTGWLARRVGELRLFVASVILFTLTSLLCGLARDLEVLVACRAL<br>QGLFSGPMVPLSQTILMRAFPPARRTLALALWGMTVLLAPIFGPVVGGWLIDNFSWPWIF<br>LINLPIGLFSFAVCTLMLRPQAQRGEASPIDAPGIVLLVIGVGSLQAMLDLGHDRGWFDS<br>PLITALAIAAGVSLVSLLIWELGEAHPVVDLSLFRERTFTFCVVIISLGMMSFSVVGVVF<br>PLWLQAVMGYTAYQAGLATASMGVLALVFSILVGLYASRVDARVLVTFGFGVFAAVMWWS<br>THFTLSMTFAQVVTPRLIQGMGLPCFFIPLTAATLSRVPDEKLAAASSLSNFLRTLSAAF<br>GTALSVTWWDNRATYHYAVVSQSVTRASENTQRYVDALHAMGLHGARELSSLHQVVRQQA<br>YMMATNDMFYMASATCLLLAGLMWLTRPKRGAAAALGH |
| 18 | MRARARRRASRCGRNERNGPQRDTGKQEGRIIRMTQTATQAATRAMIATGSRAARRLAAA<br>ALAWALAGCVPSGFEPALAPRTPGDDALAHTAGGAAHGAWPSPDWVRQLGDPQLDALVDE<br>ALRQNPTLQAAQARIGVAQSQLQQFESLTGLTATAGASLSKAHVPRSGGTINTTFNGLPV<br>SVPLVGESVVSSSSLFVGLNYQLDLWGKNAAATRGLLSMRDAARVEAEQARLALSVAIVT<br>LYGELDRAYALRELLQQKRRASEQVETVLRERAARGIDNGYDADDAALKRGKLLEQLALT<br>DEQIQLQKLQLGVLSGRGPERGLSLARPKLAPLADAPLPARLPAGLLGRRPDIVAARLRV<br>EAAYAAIDGTRASFYPDVNLAALGGLFALTPASLFKHDALGGSIGPALSLPIFDRGRLKA<br>KLGGDVANADVALALYNQTVDAALGEVARQLTSLSTVDALLEAQQQAVRSAQRMVALAQD<br>RHRRGMGMRKDVNVAKLTLLDERAHVIELQARRRTLRVGLIGALGGGFDARPAGGAPLAQ<br>GKPFAAASDRPPD |
| 19 | MRPEATDTRRHRHQRHLHRVHERFNRHRPRASKPVGPIRDGLRAGPAVAGRRHRHHARED<br>LERYRHRYPAREGAHRSGRPRRRARAARAGARARIASAAGSRGDARRAPRDAPPALRAVL<br>RAAGAGRADRGALLVRRRALQRGDGRRVRGRQRGADRRADPGDGDRRAGGGHAAGEGGAG<br>AGEARRRGRVGGVRAGAGAARAGGAAGGEHAALDGDVRGDGEGARGGPEACAAGVSGGTG<br>AAKVVAGERAGGAGGGAGAAGGGARAGQRAAGRAEPGGAAGGRAVQAGVPEPEAHDDRVA<br>GGRHGRSAVGADRSAGGAGGAADVGGAVAAGVGGGELQGRADPAHAGGPAGAARIGPVRR<br>AGDVPRPGGGGLGGHGQRVLDAAVAERGGELDQGGAAPAGGDLAGAVGAGGAPAAGGAVD<br>ARDGGDEGAWRPPARRRAAAGAAHAGARSAGGRGRGRGFGSDSGE |
| 20 | MSNKNNDELQRQASENTMGLNPVIGIRRKDLLSSARTVLRQAVRQPLHSAKHVAHFGLEL<br>KNVLLGKSSLAPDSDDRRFNDPAWSNNPLYRRYLQTYLAWRKELQDWVSSSDLSPQDISR<br>GQFVINLMTEAMAPTNTLSNPAAVKRFFETGGKSLLDGLSNLAKDMVNNGGMPSQVNMDA<br>FEVGKNLGTSEGAVVYRNDVLELIQYSPITEQVHARPLLVVPPQINKFYVFDLSPEKSLA<br>RFCLRSQQQTFIISWRNPTKAQREWGLSTYIDALKEAVDAVLSITGSKDLNMLGACSGGI<br>TCTALVGHYAALGENKVNALTVLVSVLDTTMDNQVALFVDEQTLEAAKRHSYQAGVLEGS<br>EMAKVFAWMRPNDLIWNYWVNNYLLGNEPPVFDILFWNNDTTRLPAAFHGDLIEMFKSNP<br>LTRPDALKVCGTAIDLKQVKCDIYSLAGTNDHITPWPSCYRSAHLFGGKIEFVLSNSGHI<br>QSILNPPGNPKARFMTGADRPGDPVAWQENAIKHADSWWLHWQSWLGERAGALKKAPTRL<br>GNRTYAAGEASPGTYVHER |
| 21 | MTDKPAKGSTTLPATRMNVQNAILGLRGRDLLSTLRNVGRHGLRHPLHTAHHLLALGGQL<br>GRVMLGDTPYQPNPRDARFSDPTWSQNPFYRRGLQAYLAWQKQTRQWIDESHLNDDDRAR<br>AHFLFNLINDALAPSNSLLNPQAVKGLFNTGGQSLVRGVAHLLDDLRHNDGLPRQVDERA<br>FEVGVNLAATPGAVVFRNELLELIQYSPMSEKQHARPLLVVPPQINRFYIFDLSATNSFV<br>QYMLKSGLQVFMVSWSNPDPRHREWGLSSYVQALEEALNACRSISGNRDPNLMGACAGGL<br>TMAALQGHLQAKKQLRRVRSATYLVSLLDSKFESPASLFADEQTIEAAKRRSYQRGVLDG<br>GEVARIFAWMRPNDLIWNYWVNNYLLGKTPPAFDILYWNADSTRLPAALHGDLLEFFKLN<br>PLTYASGLEVCGTPIDLQQVNIDSFTVAGSNDHITPWDAVYRSALLLGGERRFVLANSGH<br>IQSIINPPGNPKAYYLANPKLSSDPRAWFHDAKRSEGSWWPLWLEWITARSGLLKAPRTE<br>LGNATYPLLGPAPGTYVLTR |
| 22 | MRPEIAVLDIQGQYRVYTEFYRADAAENTIILINGSLATTASFAQTVRNLHPQFNVVLFD<br>QPYSGKSKPHNRQERLISKETEAHILLELIEHFQADHVMSFSWGGASTLLALAHQPRYVK |

TABLE 1-continued

Sequences of the enzymes used according to any aspect
of the present invention.

| SEQ ID NO | SEQUENCE |
|---|---|
|  | KAVVSSFSPVINEPMRDYLDRGCQYLAACDRYQVGNLVNDTIGKHLPSLLKRFNYRHVSS<br>LDSHEYAQMHFHINQVLEHDLERALQGARNINIPVLFINGERDEYTTVEDARQFSKHVGR<br>SQFSVIRDAGHFLDMENKTACENTRSVMLGFLKPTVREPRQRYQPVQQGQHALAI |
| 23 | MRPETAIIEIHGQYRIHTEFYGNPAAQQTIILVNGSLSTTASFAQTVKYLQPHYNVVLYD<br>QPYAGQSKPHNENHTPISKECEARILLELIERFRAEVVMSFSWGGVATLLALAQRPGRIR<br>RAVVNSFSPQLNPAMLDYLHRGLDYLAACDRTQIGNLVNETIGRYLPQLFKRYNFRHVSS<br>LDEHEYHQMHFHIREVLRLNADSYTESFAGIEIPMLFMNGELDIYTTPHEARQFGQLIRG<br>AEFHTIRNAGHFIDVEHKAAWQQTQDALLAFLRPQRTQPLNPIYRPQPNGASVPLAALAS |

BRIEF DESCRIPTION OF THE FIGURES

FIG. 1 is a graph illustrating the composition by percentage of the rhamnolipid products formed depending on the different carbon sources.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

In the production of rhamnolipids by *Pseudomonas putida*, before the product concentration in the different examples is determined, the reaction samples were diluted immediately after fermentation with acetone at a volume ratio of 1:1 and centrifuged at 21,000 g and 4° C. for 2 min. The sample supernatant was then measured by HPLC.

Example 1 (A Comparative Example, not of the Invention)

Production of Rhamnolipids with BS-PP-001 from Glucose

On an LB agar plate containing 50 mg/l kanamycin an inoculation loop of glycerol cryoculture of the strain *Pseudomonas putida* KT2440 pBBR1MCS-2::ABC (BS-PP-001) was streaked. The method of producing the vector pBBR1 MCS-2::ABC is provided in Example 2 of DE102010032484A1. The *Pseudomonas putida* is then transformed with the vector and stored. The agar plate was incubated for 24 h at 30° C. A 100 ml flask with baffles containing 25 ml of LB medium with kanamycin was inoculated with a single culture of overgrown agar plate and incubated in a shaking incubator for 24 h at 30° C. and 200 rpm to produce a preculture. The preculture was centrifuged at 5500 g at room temperature for 10 minutes. The supernatant was then discarded. The pellet was resuspended in 25 ml of M9 medium (composition: 6.8 g/l $Na_2PO_4.2H_2O$, 2.4 g/l $KH_2PO_4$, 0.4 g/l NaCl, 1.6 g/l $NH_4Cl$, 0.5 g/l $MgSO_4.7H_2O$, 1 ml of trace element solution US3, consisting of 36.5 g/l of 37% strength hydrochloric acid, 1.91 g/l $MnCl_2.4H_2O$, 1.87 g/l $ZnSO_4.7H_2O$, 0.84 g/l $Na_2EDTA.2H_2O$, 0.3 g/l $H_3BO_3$, 0.25 g/l $Na_2MoO_4.2H_2O$, 4.7 g/l $CaCl_2.2H_2O$, 17.3 g/l $FeSO_4.7H_2O$, 0.15 g/l $CuCl_2.2H_2O$). This washing step was then repeated.

In a 300 ml fermenter, 180 ml of M9 medium as described above was added with 20 g/l glucose and with 50 mg/l kanamycin. The fermenter was inoculated with a large volume of preculture suspension to reach a start $OD_{600}$ of 0.4. The following parameters were set during fermentation: gassing with air 2 NL/h, dissolved oxygen concentration adjusted to 30% by adjusting the stirrer speed. This measurement is carried out using a standard oxygen sensor, temperature of 30° C., initial pH value of 7.4 (not regulated throughout the experiment). After 40 h of fermentation, glucose solution (concentration in the fermenter of: 15 g/l) was fed via a syringe. At specified times, samples were taken from the fermenter to determine the concentration of rhamnolipids and fatty acid dimers produced.

The results are shown in Table 2 below and FIG. 1.

Example 2

Production of Rhamnolipids with BS-PP-001 from Butyric Acid

The preculture was made analogously to Example 1 with glucose.

In a 300 ml fermenter, 180 ml of M9 medium as described in Example 1 was added with 6.5 g/l sodium butyrate and 50 mg/l kanamycin. The fermenter was inoculated with a large volume of preculture suspension to reach a start $OD_{600}$ of 0.4. The following parameters were set during fermentation: gassing with air 2 NL/h, stirrer speed set at 300 rpm, temperature 30° C., initial pH value of 7.4 (not regulated throughout the experiment). After 40 h of fermentation, sodium butyrate solution (concentration in the fermenter: 5 g/l butyric acid) was fed via a syringe. The stirrer speed was increased to 900 rpm.

At specified times, samples were taken from the fermenter to determine the concentration of rhamnolipids and fatty acid dimers produced.

The results are shown in Table 2 below and FIG. 1.

Example 3

Production of Rhamnolipids Using BS-PP-001+alkB from n-Butane

On an LB agar plate containing 50 mg/l kanamycin, an inoculation loop full of glycerol cryoculture of the strain *P. putida* pBBR1 MCS-2::ABC pBT10 was (BS-PP001+alkB) streaked. This strain was produced by adding to the strain of Example 1 the gene construct pBT10 as described on pages 36 and 37 (SEQ-ID 31) of WO2009/077461A1. The agar plate was incubated for 24 h at 30° C.

Three 100 ml flasks with baffles was filed with 25 ml of LB medium containing kanamycin and each inoculated with a single culture of the overgrown agar plate and incubated in a shaking incubator for 24 h at 30° C. and 200 rpm.

Three 1-liter flasks with baffles were each used to mix 75 ml of modified M9 medium (composition: 15 g/l glucose, 6.8 g/l $Na_2PO_4$, 3 g/l $KH_2PO_4$, 0.5 g/l NaCl, 2 g/l $NH_4Cl$, 15 g/l yeast extract, 0.49 g/l $MgSO_4 \times 7H_2O$, 50 mg/l kanamycin sulfate, 15 ml trace element solution US3 consisting of 36.5 g/l of 37% strength hydrochloric acid, 11.91 g/l $MnCl_2.4H_2O$, 1.87 g/l $ZnSO_4.7H_2O$, 0.84 g/l Na-$EDTA.2H_2O$, 0.3 g/l $H_3BO_3$, 0.25 g/l $Na_2MoO_4.2H_2O$, 4.7 g/l $CaCl_2.2H_2O$, 17.3 g/l $FeSO_4.7H_2O$, 0.15 g/l $CuCl_2.2H_2O$) and the preculture from the 100 ml flasks. The cultures were incubated at 30° C. and 200 rpm. After 3 hours of incubation alkBGT genes was activated by adding 0.4 mM of dicyclopropylketone. The cultures were incubated for a further 16 h at 25° C. and 200 rpm.

The cultures in the three flasks were combined and centrifuged at 5500 g at room temperature for 10 minutes. The supernatant was discarded. The pellet was resuspended in 25 ml of M9 medium (composition of which is provided above). This washing step was repeated for the removal of glucose and other possible carbon sources.

In a 300 ml fermenter, 180 ml of M9 medium (composition of which is provided above without a carbon source), 50 mg/l 50 mg/l kanamycin were added. The fermenter was inoculated with a large volume of preculture suspension from the earlier step to reach a start $OD_{600}$ of 10. The following parameters were set during fermentation: gassing with butane/air mixture (25%/75%) 2 NL/h, stirrer speed set at 900 rpm, temperature 30° C., initial pH value of 7.4 (not regulated throughout the experiment). At specified times, samples were taken from the fermenter to determine the concentration of rhamnolipids and fatty acid dimers produced.

The results are shown in Table 2 below and FIG. 1.

TABLE 2

Final concentrations of rhamnolipids and fatty acid dimers produced based on the substrate used.

| Strain, Substrate | Rhamno-lipid-2 2RL [mg/l] | Rhamno-lipid-1 1RL [mg/l] | Fatty Acid dimers (FA-dimer) [mg/l] | Total [mg/l] |
|---|---|---|---|---|
| BS-PP-001, Glucose | 110 | 81 | 793 | 983 |
| BS-PP-001, Butyrate | 29 | 343 | 538 | 910 |
| BS-PP-001 + AlkB, Butane | 438 | 58 | 0 | 496 |
| BS-PP-001 + AlKB, 1-Butanol | 1.146 | 142 | 0 | 1.288 |

As can be seen, Table 2 shows that the strain equipped with the genes rhlA, rhlB and rhlC from *P. aeruginosa* of the species *P. putida* KT2440 (BS-PP-001) was able to produce about 1 g/l of products, of which about 110 mg/l were dirhamnolipid and 81 mg/l were monorhamnolipid, as well as almost 800 mg of unwanted fatty acid dimers when glucose was used as a substrate.

When butyrate was used as the sole carbon source, the amount of dirhamnolipid significantly increased, while only about one-third of unwanted fatty acid dimers were formed. In another example, a strain was genetically modified to introduce oxidoreductase AlkB from *Pseudomonas putida* GPO1 and fed with butane as the sole carbon source. The results provided in Table 2 showed that up to over 1000 mg/l of dirhamnolipid was formed and no measurable amounts of undesirable fatty acid dimers were produced.

The results in FIG. 1 also illustrate composition by percentage of the product formed depending on the different carbon sources. It can be seen that the use of butyrate reduces the amount of unwanted fatty acid dimers from 81% to 64%, and with the use of butane and butanol, the amount of fatty acid dimers formed is not measurable.

Example 4

Production of Rhamnolipids Using BS-PP-001+alkB from 1-Butanol

Three 100 ml flasks with baffles were filled with 25 ml of LB medium containing kanamycin and tetracyclin and each inoculated with 100 µl of a glycerol cryoculture of the strain *P. putida* pBBR1MCS-2::ABC pBT10 (BS-PP001+alkB). This strain was produced by adding to the strain of Example 1 the gene construct pBT10 as described on pages 36 and 37 (SEQ-ID 31) of WO2009/077461A1. The flasks were incubated in a shaking incubator for 24 h at 30° C. and 200 rpm.

Three 1-liter flasks with baffles were each used to mix 75 ml of modified M9 medium (composition: 15 g/l glucose, 6.8 g/l $Na_2PO_4$, 3 g/l $KH_2PO_4$, 0.5 g/l NaCl, 2 g/l $NH_4Cl$, 15 g/l yeast extract, 0.49 g/l $MgSO_4 \times 7H_2O$, 50 mg/l kanamycin sulfate, 10 mg/l tetracycline, 15 mil/l trace element solution US3 consisting of 36.5 g/l of 37% strength hydrochloric acid, 11.91 g/l $MnCl_2.4H_2O$, 1.87 g/l $ZnSO_4.7H_2O$, 0.84 g/l Na-$EDTA.2H_2O$, 0.3 g/l $H_3BO_3$, 0.25 g/l $Na_2MoO_4.2H_2O$, 4.7 g/l $CaCl_2.2H_2O$, 17.3 g/l $FeSO_4.7H_2O$, 0.15 g/l $CuCl_2.2H_2O$) and the preculture from the 100 ml flasks. The cultures were incubated at 30° C. and 200 rpm. After 3 hours of incubation alkBGT genes was activated by adding 0.4 mM of dicyclopropylketone. The cultures were incubated for a further 4 h at 30° C. and 200 rpm.

The cultures in the three flasks were combined and centrifuged at 5500 g at room temperature for 10 minutes. The supernatant was discarded. The pellet was resuspended in 25 ml of M9 medium (composition of which is provided above). This washing step was repeated for the removal of glucose and other possible carbon sources.

In a 300 ml fermenter, 180 ml of M9 medium (composition of which is provided above without a carbon source), 50 mg/l kanamycin were added. The fermenter was inoculated with 10 ml of preculture suspension from the earlier step to reach a start $OD_{600}$ of 5. The following parameters were set during fermentation: gassing with air 3 Nl/h, stirrer speed set at 700 rpm, temperature 30° C., pH value of 7.0 (regulated throughout the experiment with 5% ammonia solution). Butanol solution was fed via a syringe (feed rate 0.2 g/l (1 h)). At specified times, samples were taken from the fermenter to determine the concentration of rhamnolipids and fatty acid dimers produced.

The results are provided in Table 2 above.

REFERENCES

1. *Handbook of Hydrocarbon and Lipid Microbiology*, 2010, pages 3037-51
2. Leitermann et al., 2009
3. Hermann et al., (Electrophoresis, 22: 1712.23 (2001)
4. Sambrook et al., Molecular Cloning: a laboratory manual, 2nd Ed. Cold Spring Harbor Laboratory Press, Cold Spring Harbor, N.Y. USA, 1989
5. Lohaus and Meyer (1989) Biospektrum, 5: 32-39; Lottspeich (1999) Angewandte Chemie 111: 2630-2647
6. Wilson et al. (2001) Journal of Bacteriology, 183: 2151-2155

7. Donahue et al. (2000) Journal of Bacteriology 182 (19): 5624-5627
8. Ray et al. (2000) Journal of Bacteriology 182 (8): 2277-2284
9. Freedberg et al. (1973) Journal of Bacteriology 115 (3): 816-823
10. Lohaus et al., Biospektrum 5 32-39 (1998),
11. Lottspeich, Angewandte Chemie 111:2630-2647 (1999)
12. Wilson et al., Journal of Bacteriology 183: 2151-2155 (2001)
13. Martin et al. Bio/Technology 5, 137-146 (1987)
14. Guerrero et al. Genes 138, 35-41 (1994)
15. Tsuchlya and Morinaga Bio/Technology 6, 428-430 (1988)
16. Eikmanns et al. Genes 102, 93-98 (1991))
17. Schwarzer and Pühler Bio/Technology 9, 84-87 (1991),
18. Reinscheld et al. Applied and Environmental Microbiology 60, 126-132 (1994),
19. LaBarre et al. Journal of Bacteriology 175, 1001-1007 (1993),
20. Malumbres et al. Genes 134, 15-24 (1993),
21. Jensen and Hammer Biotechnology and Bioengineering 58, 191-195 (1998)
22. Glover, D. M. (1985) DNA cloning: a practical approach, Vol. I-III, IRL Press Ltd., Oxford;
23. Rodriguez, R. L. and Denhardt, D. T (eds) (1988) Vectors: a survey of molecular cloning vectors and their uses, 179-204, Butterworth, Stoneham
24. Goeddel, D. V. (1990) Systems for heterologous gene expression, Methods Enzymol. 185, 3-7
25. Sambrook, J.; Fritsch, E. F. and Maniatis, T. (1989), Molecular cloning: a laboratory manual, 2nd ed., Cold Spring Harbor Laboratory Press, New York
26. Schäfer et al., Applied and Environmental Microbiology 60: 756-759 (1994)
27. Thierbach et al., Applied Microbiology and Biotechnology 29: 356-362 (1988)
28. Dunican and Shivnan, Bio/Technology 7:1067-1070 (1989)
29. Tauch et al., FEMS Microbiology Letters 123: 343-347 (1994)
30. De Eugenio et al., Environ Microbiol. 2010. 12(1):207-21
31. Rehm et al., Appl Environ Microbiol. 2001. 67(7): 3102-9
32. Dubeau et al. 2009. BMC Microbiology 9:263
33. Singh & Röhm. Microbiology. 2008. 154:797-809
34. Lee et al. FEMS Microbiol Lett. 2009. 297(1):38-48
35. Ren et al., Journal Applied Microbiology and Biotechnology 1998 June, 49(6):743-50,
36. Huisman et al., J Biol Chem. 1991 Feb. 5; 266(4):2191-8
37. De Eugenio et al., Environ Microbiol. 2010. 12(1):207-21
38. Ouyang et al. Macromol Biosci. 2007. 7(2):227-33
39. "Bioprozesstechnik 1. Einführung in die Bioverfahrenstechnik" [Bioprocess Technology 1. Introduction to the Bioprocess Technique] (Gustav Fischer Verlag, Stuttgart, 1991))
40. "Bioreaktoren und periphere Einrichtungen" [Bioreactors and Peripheral Devices], Vieweg Verlag, Brunswick/Wesbaden, 1994
41. "Nonconventional yeast in biotechnology" (Ed. Klaus Wolf, Springer-Verlag Berlin, 1996)
42. Scheps, D., Malca, H., Hoffmann, B., Nestl, B. M, und Hauer, B. (2011) Org. Biomol. Chem., 9, 6727
43. WO2012013554A1, DE-A-10031999, GB-A-1009370, EP-A-0 472 869, U.S. Pat. No. 4,601,893, WO-A-96/15246, JP-A-10-229891, WO2009/077461A1
44. Burger, M. M., et al., 1963. J. Biol. Chem. 238:2595-2602.
45. Burger, M. M., et al., 1966. Methods Enzymol. 8:441-445.

The invention claimed is:

1. A method of preparing at least one rhamnolipid comprising:
   a) contacting a recombinant cell with a medium containing a carbon source wherein the recombinant cell has been genetically modified such that, compared to the wild-type of the cell, said recombinant cell has increased activity of all three of enzymes $E_1$, $E_2$ and $E_3$, and wherein:
      i) enzyme $E_1$ comprises the sequence of SEQ ID NO:2 or an enzyme comprising a sequence in which up to 10% of the amino acids of SEQ ID NO:2 have been modified and for which more than 50% of the enzymatic activity of SEQ ID NO:2 in converting 3-hydroxy-decanoyl-ACP via 3-hydroxydecanoyl-3-hydroxydecanoic acid-ACP to hydroxydecanoyl-3-hydroxydecanoic acid is maintained;
      ii) enzyme $E_2$ comprises the sequence of SEQ ID NO:7 or an enzyme comprising a sequence in which up to 10% of the amino acids of SEQ ID NO:7 have been modified and for which more than 50% of the enzymatic activity of SEQ ID NO:7 in converting dTDP-rhamnose and 3-hydroxydecanoyl-3-hydroxydecanoic acid to a-L-rhamnopyranosyl-3-hydroxydecanoyl-3-hydroxydecanoic acid is maintained;
      ii) enzyme $E_3$ comprises the sequence of SEQ ID NO:12 or an enzyme comprising a sequence in which up to 10% of the amino acids of SEQ ID NO:12 have been modified and for which more than 50% of the enzymatic activity of SEQ ID NO:12 in converting dTDP rhamnose and a-L-rhamnopyranosyl-3-hydroxydecanoyl-3-hydroxydecanoic acid to a-L-rhamnopyranosyl-(1-2)-a-L-rhamnopyranosyl-3-hydroxydecanoyl-3-hydroxydecanoic acid is maintained;
   b) culturing the recombinant cell under suitable conditions for preparation of the rhamnolipid from the carbon source by the cell;
   c) optionally isolating rhamnolipids from the cells and/or the medium of step b);
   wherein at least 70% of the total carbon content of the medium in which the recombinant cells are cultured is in the form of $C_4$ molecules having exactly four carbon atoms.

2. The method of claim 1, wherein the $C_4$ molecules have no atoms other than carbon, oxygen and hydrogen.

3. The method of claim 1, wherein the $C_4$ molecule is selected from the group consisting of: butane; 1-butanol; 2-butanol; 1-butanal; butanone; butyric acid; and combinations thereof.

4. The method of claim 3, wherein at least 90% of the total carbon content of the medium in which the recombinant cells are cultured is in the form of butane; 1-butanol; 2-butanol; 1-butanal; butanone; butyric acid; or combinations thereof.

5. The method of claim 3, wherein at least 90% of the total carbon content of the medium in which the recombinant cells are cultured is in the form of butyric acid or butane.

6. The method of claim 3, wherein 100% of the total carbon content of the medium in which the recombinant cells are cultured is in the form of butane; 1-butanol; 2-butanol; 1-butanal; butanone; butyric acid; or combinations thereof.

7. The method of claim 1, wherein the recombinant cell has been genetically modified such that, compared to the wild-type cell, there is increased activity of an oxidoreductase.

8. The method of claim 7, wherein the oxidoreductase is selected from the group consisting of: alkB-type oxidoreductase; monooxygenase; and NAD(P)H dependent alcohol dehydrogenase (ADH).

9. The method according of claim 1, wherein said cell is selected from a genus of the group consisting of: *Aspergillus*; *Corynebacterium*; *Brevibacterium*; *Bacillus*; *Acinetobacter*; *Alcaligenes*; *Lactobacillus*; *Paracoccus*; *Lactococcus*; *Candida*; *Pichia*; *Hansenula*; *Kluyveromyces*; *Saccharomyces*; *Escherichia*; *Zymomonas*; *Yarrowia*; *Methylobacterium*; *Ralstonia*; *Pseudomonas*; *Rhodospirillum*; *Rhodobacter*; *Burkholderia*; *Clostridium*; and *Cupriavidus*.

10. The method of claim 1, wherein said cell is selected from the group consisting of: *P. putida* GPp121; *P. putida* GPp122; *P. putida* GPp123; *P. putida* GPp124; *P. putida* GPp104, *P. putida* KT42C1, *P. putida* KTOY01 and *P. putida* KTOY02.

11. The method of claim 1, wherein the rhamnolipid comprises the general formula (I),

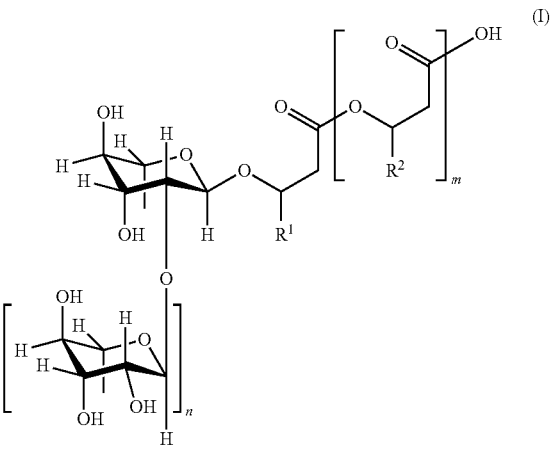

wherein:
m=2, 1 or 0;
n=1 or 0; and
$R^1$ and $R^2$=independently of one another, identical or different organic radicals having 2 to 24 carbons.

12. The method of claim 11, wherein, in formula I, one or both of the organic radicals are branched and/or substituted.

13. The method of claim 11, wherein, in formula I, one or both of the organic radicals are unsaturated.

14. The method of claim 11, wherein, in formula I, m=1 or 0 and n=1.

15. The method of claim 1, wherein enzyme $E_1$ consists of the amino acid sequence of SEQ ID NO:2.

16. The method of claim 15, wherein enzyme $E_2$ consists of the amino acid sequence of SEQ ID NO:7.

17. The method of claim 16, wherein enzyme $E_3$ consists of the amino acid sequence of SEQ ID NO:12.

18. The method of claim 17, wherein said cell is selected from the group consisting of: *P. putida* GPp121; *P. putida* GPp122; *P. putida* GPp123; *P. putida* GPp124; *P. putida* GPp104, *P. putida* KT42C1, *P. putida* KTOY01 and *P. putida* KTOY02.

19. The method of claim 18, wherein at least 90% of the total carbon content of the medium in which the recombinant cells are cultured is in the form of butane; 1-butanol; 2-butanol; 1-butanal; butanone; butyric acid; or combinations thereof.

20. The method of claim 18, wherein 100% of the total carbon content of the medium in which the recombinant cells are cultured is in the form of butane; 1-butanol; 2-butanol; 1-butanal; butanone; butyric acid; or combinations thereof.

* * * * *

SEQUENCE LISTING

```
<160> NUMBER OF SEQ ID NOS: 23

<210> SEQ ID NO 1
<211> LENGTH: 399
<212> TYPE: PRT
<213> ORGANISM: Pseudomonas putida
<220> FEATURE:
<221> NAME/KEY: SITE
<222> LOCATION: (1)..(399)
<223> OTHER INFORMATION: alkB-type oxidoreductase

<400> SEQUENCE: 1

Glu Lys His Arg Val Leu Asp Ser Ala Pro Glu Tyr Val Asp Lys Lys
1               5                   10                  15

Lys Tyr Leu Trp Ile Leu Ser Thr Leu Trp Pro Ala Thr Pro Met Ile
            20                  25                  30

Gly Ile Trp Leu Ala Asn Glu Thr Gly Trp Gly Ile Phe Tyr Gly Leu
        35                  40                  45

Val Leu Leu Val Trp Tyr Gly Ala Leu Pro Leu Leu Asp Ala Met Phe
    50                  55                  60

Gly Glu Asp Phe Asn Asn Pro Pro Glu Glu Val Val Pro Lys Leu Glu
65                  70                  75                  80

Lys Glu Arg Tyr Arg Val Leu Thr Tyr Leu Thr Val Pro Met His
            85                  90                  95

Tyr Ala Ala Leu Ile Val Ser Ala Trp Trp Val Gly Thr Gln Pro Met
```

-continued

```
                100                 105                 110
        Ser Trp Leu Glu Ile Gly Ala Leu Ala Leu Ser Leu Gly Ile Val Asn
                    115                 120                 125

Gly Leu Ala Leu Asn Thr Gly His Glu Leu Gly His Lys Lys Glu Thr
                    130                 135                 140

Phe Asp Arg Trp Met Ala Lys Ile Val Leu Ala Val Val Gly Tyr Gly
        145                 150                 155                 160

His Phe Phe Ile Glu His Asn Lys Gly His His Arg Asp Val Ala Thr
                            165                 170                 175

Pro Met Asp Pro Ala Thr Ser Arg Met Gly Glu Ser Ile Tyr Lys Phe
                        180                 185                 190

Ser Ile Arg Glu Ile Pro Gly Ala Phe Ile Arg Ala Trp Gly Leu Glu
                        195                 200                 205

Glu Gln Arg Leu Ser Arg Arg Gly Gln Ser Val Trp Ser Phe Asp Asn
                    210                 215                 220

Glu Ile Leu Gln Pro Met Ile Ile Thr Val Ile Leu Tyr Ala Val Leu
        225                 230                 235                 240

Leu Ala Leu Phe Gly Pro Lys Met Leu Val Phe Leu Pro Ile Gln Met
                            245                 250                 255

Ala Phe Gly Trp Trp Gln Leu Thr Ser Ala Asn Tyr Ile Glu His Tyr
                        260                 265                 270

Gly Leu Leu Arg Gln Lys Met Glu Asp Gly Arg Tyr Glu His Gln Lys
                    275                 280                 285

Pro His His Ser Trp Asn Ser Asn His Ile Val Ser Asn Leu Val Leu
                290                 295                 300

Phe His Leu Gln Arg His Ser Asp His Ala His Pro Thr Arg Ser
        305                 310                 315                 320

Tyr Gln Ser Leu Arg Asp Phe Pro Gly Leu Pro Ala Leu Pro Thr Gly
                        325                 330                 335

Tyr Pro Gly Ala Phe Leu Met Ala Met Ile Pro Gln Trp Phe Arg Ser
                    340                 345                 350

Val Met Asp Pro Lys Val Val Asp Trp Ala Gly Gly Asp Leu Asn Lys
                    355                 360                 365

Ile Gln Ile Asp Asp Ser Met Arg Glu Thr Tyr Leu Lys Lys Phe Gly
                370                 375                 380

Thr Ser Ser Ala Gly His Ser Ser Thr Ser Ala Val Ala Ser
        385                 390                 395

<210> SEQ ID NO 2
<211> LENGTH: 295
<212> TYPE: PRT
<213> ORGANISM: Pseudomonas sp.
<220> FEATURE:
<221> NAME/KEY: SITE
<222> LOCATION: (1)..(295)
<223> OTHER INFORMATION: enzyme E1a

<400> SEQUENCE: 2

Met Arg Arg Glu Ser Leu Leu Val Ser Val Cys Lys Gly Leu Arg Val
        1               5                   10                  15

His Val Glu Arg Val Gly Gln Asp Pro Gly Arg Ser Thr Val Met Leu
                        20                  25                  30

Val Asn Gly Ala Met Ala Thr Thr Ala Ser Phe Ala Arg Thr Cys Lys
                    35                  40                  45

Cys Leu Ala Glu His Phe Asn Val Val Leu Phe Asp Leu Pro Phe Ala
                50                  55                  60
```

```
Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295

<210> SEQ ID NO 3
<211> LENGTH: 346
<212> TYPE: PRT
<213> ORGANISM: Burkholderia sp.
<220> FEATURE:
<221> NAME/KEY: SITE
<222> LOCATION: (1)..(346)
<223> OTHER INFORMATION: enzyme E1b

<400> SEQUENCE: 3

Met Arg Gly Ser Gly Glu Trp Val Ala Ala Ala Ala Arg Val Arg Gln
1               5                   10                  15

Gly Gly Gln Ile Ala Arg Glu Gly Gly Tyr Val Glu Ala Ser Ile Lys
            20                  25                  30

Gly Ala Gly Ser Ala His Leu Pro Ser Arg Cys Gly Arg Tyr Ala Met
        35                  40                  45

Pro Ile Glu Lys Gln Val Val Ala Leu Pro Ser Gly Leu Lys Val His
    50                  55                  60

Val Glu Arg His Val Phe Asp Pro Ala Phe Glu Thr Val Ile Leu Val
65                  70                  75                  80

Asn Gly Ala Leu Ala Thr Thr Ala Ser Phe Gly Gln Thr Ile Arg Tyr
                85                  90                  95

Leu Gly Glu Arg Val Asn Ala Val Cys Phe Asp Leu Pro Tyr Ala Gly
            100                 105                 110
```

```
Gln Ser Arg Gln His Asn Pro Gly Glu Tyr Ile Leu Thr Lys Asp Asp
            115                 120                 125

Glu Val Glu Ile Leu Leu His Leu Ala Glu Arg Phe Glu Pro Ser Phe
130                 135                 140

Leu Leu Ser Val Ser Trp Gly Val Ala Ser Leu Phe Ala Leu Ala
145                 150                 155                 160

Arg Gly Cys Ala Ser Val Arg Arg Ala Val Ile Ala Ser Phe Ser Pro
                165                 170                 175

Phe Leu Asn Asp Ala Met Thr Asp Tyr Val Thr Arg Ala Arg Asp His
            180                 185                 190

Ile Ala Ala Gly Glu Asn Leu Lys Ala Ala Gln Leu Leu Asn Asp Thr
        195                 200                 205

Val Gly Arg Tyr Leu Pro Arg Ile Met Lys Leu Tyr Asn Tyr Arg Tyr
210                 215                 220

Leu Thr Lys Leu Pro Arg Thr Glu Gln Asp Gln Val Ala Phe His Val
225                 230                 235                 240

Asp Gln Ile Leu Ser Met Arg Pro Glu Gln Tyr Leu Pro Glu Phe Arg
                245                 250                 255

Gln Ile Gly Cys Ala Val Lys Phe Ile Asn Gly Glu Leu Asp Glu Tyr
            260                 265                 270

Thr Thr Ala Ser Asp Val Arg Arg Leu Ala Ala Tyr Val Arg Arg Ala
        275                 280                 285

Glu Phe Ala Thr Ile Arg Gln Ala Gly His Phe Leu Asp Leu Glu Gly
    290                 295                 300

Arg Gln Gln Gln Glu Gln Leu Arg Ala Ala Ile Leu Gly Phe Phe Gly
305                 310                 315                 320

Asp Glu Arg Ala Ser Ala Ala Arg Asp Ala Gln Asp Glu Thr Leu
                325                 330                 335

Ala Pro Leu Gly Gln Leu Pro Ala Leu Ser
            340                 345

<210> SEQ ID NO 4
<211> LENGTH: 295
<212> TYPE: PRT
<213> ORGANISM: Pseudomonas sp.
<220> FEATURE:
<221> NAME/KEY: SITE
<222> LOCATION: (1)..(295)
<223> OTHER INFORMATION: enzyme E1c

<400> SEQUENCE: 4

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
```

```
            115                 120                 125
Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295

<210> SEQ ID NO 5
<211> LENGTH: 295
<212> TYPE: PRT
<213> ORGANISM: Pseudomonas sp.
<220> FEATURE:
<221> NAME/KEY: SITE
<222> LOCATION: (1)..(295)
<223> OTHER INFORMATION: enzyme E1d

<400> SEQUENCE: 5

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Gln Arg Leu Lys Ala Ser Asn His Gln
                165                 170                 175
```

```
His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
210                 215                 220

Tyr Thr Thr Ala Glu Asp Ala Arg Gln Phe Arg Asp Tyr Leu Pro His
225                 230                 235                 240

Cys Ser Phe Ser Arg Val Gly Thr Gly His Phe Leu Asp Leu Glu
            245                 250                 255

Ser Lys Leu Ala Ala Val Arg Val His Arg Ala Leu Leu Glu His Leu
                260                 265                 270

Leu Lys Gln Pro Glu Pro Gln Arg Ala Glu Arg Ala Ala Gly Phe His
            275                 280                 285

Glu Met Ala Ile Gly Tyr Ala
    290                 295

<210> SEQ ID NO 6
<211> LENGTH: 295
<212> TYPE: PRT
<213> ORGANISM: Pseudomonas sp.
<220> FEATURE:
<221> NAME/KEY: SITE
<222> LOCATION: (1)..(295)
<223> OTHER INFORMATION: enzyme E1e

<400> SEQUENCE: 6

Met Arg Arg Glu Ser Leu Leu Val Thr Val Cys Lys Gly Leu Arg Val
1               5                   10                  15

His Val Glu Arg Val Gly Gln Asp Pro Gly Arg Asp Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Ala Val Asn
            85                  90                  95

His Leu Val Ser Ala Ser Trp Gly Gly Ile Ser Thr Leu Leu Ala Leu
            100                 105                 110

Ser Arg Asn Pro Arg Gly Val Arg Ser Ser Val Val Met Ala Phe Ala
        115                 120                 125

Pro Gly Leu Asn Gln Ala Met Leu Asp Tyr Val Gly Arg Ala Gln Glu
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ser Cys Leu
        195                 200                 205

Gly Gln Ile Gln Ser His Val His Phe Ile Asn Gly Ser Trp Asp Glu
    210                 215                 220
```

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
            245                 250                 255

Ser Lys Leu Ala Ala Ala Arg Val His Arg Ala Leu Leu Glu His Leu
        260                 265                 270

Leu Ala Gln Pro Glu Pro Trp Arg Ser Glu Gln Ala Ala Gly Phe His
    275                 280                 285

Glu Met Ala Ile Gly Tyr Ala
    290             295

<210> SEQ ID NO 7
<211> LENGTH: 426
<212> TYPE: PRT
<213> ORGANISM: Pseudomonas sp.
<220> FEATURE:
<221> NAME/KEY: SITE
<222> LOCATION: (1)..(426)
<223> OTHER INFORMATION: Enzyme E2a

<400> SEQUENCE: 7

Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Asp Ala Val Glu Gln His Gly Ile
            35                  40                  45

Ala Phe Val Pro Leu Ser Asp Glu Leu Thr Tyr Arg Arg Thr Met Gly
    50                  55                  60

Asp Pro Arg Leu Trp Asp Pro Lys Thr Ser Phe Gly Val Leu Trp Gln
65                  70                  75                  80

Thr Ile Ala Gly Met Ile Glu Pro Val Tyr Glu Tyr Val Ser Ala Gln
                85                  90                  95

Arg His Asp Asp Ile Val Val Gly Ser Leu Trp Ala Leu Gly Ala
            100                 105                 110

Arg Ile Ala His Glu Lys Tyr Gly Ile Pro Tyr Leu Ser Ala Gln Val
            115                 120                 125

Ser Pro Ser Thr Leu Leu Ser Ala His Leu Pro Pro Val His Pro Lys
    130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Asp Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly

```
                275                 280                 285
Ala Gly Gln Glu Pro Leu Arg Gly Leu Pro Asn His Val Leu Gln Arg
        290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
                340                 345                 350

Arg Leu Val Arg Leu Gly Cys Gly Met Arg Leu Gly Val Pro Leu Arg
                355                 360                 365

Glu Gln Glu Leu Arg Gly Ala Leu Trp Arg Leu Leu Glu Asp Pro Ala
        370                 375                 380

Met Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                405                 410                 415

Gly Asp Ala Arg Trp Leu Lys Ala Ala Ser
                420                 425

<210> SEQ ID NO 8
<211> LENGTH: 493
<212> TYPE: PRT
<213> ORGANISM: Burkholderia sp.
<220> FEATURE:
<221> NAME/KEY: SITE
<222> LOCATION: (1)..(493)
<223> OTHER INFORMATION: Enzyme E2b

<400> SEQUENCE: 8

Met Asp Ala Gly Arg Ile Gly Leu His Asp Ala Ala Ala Gly Arg
1               5                   10                  15

Ile Gly Met Thr Glu Ala Phe Ala Ser Arg Ala Arg Cys Ser Ala Ala
                20                  25                  30

Ala Leu Ala Ala Gly Gly Arg Ala Pro Ala Gly Asp Gly Arg Ser Gly
            35                  40                  45

Ser Asn Arg Ala Ala Ala Asn Gly Ser Val Asp Cys Arg Ala Gly Trp
    50                  55                  60

Asn Asp Glu Ala Met Ala Lys Val Ile Val Thr Ala Ile Gly Ser Ala
65                  70                  75                  80

Gly Asp Val His Pro Leu Leu Gly Val Ser Arg Ala Leu Ser Ala Arg
                85                  90                  95

Gly His Glu Val Val Phe Cys Thr His Ala Pro Phe Glu Ala Ala Val
                100                 105                 110

Arg Ala Ser Gly Phe Ala Phe Val Pro Val Gly Thr Ala Glu Asp Tyr
            115                 120                 125

Val Arg Ala Met Ala Asp Pro Ala Leu Trp Asp Pro Arg Thr Ser Phe
    130                 135                 140

Lys Thr Leu Trp Arg Val Ile Ala Pro Val Val Arg Pro His Phe Glu
145                 150                 155                 160

Val Leu Arg Ala Leu Ser Asp Ala Asp Thr Val Leu Val Gly Thr Leu
                165                 170                 175

Trp Ala Phe Ser Ala Arg Leu Met Gln Glu Arg Phe Gly Thr Arg Tyr
                180                 185                 190

Val Ser Val Gln Val Ser Pro Ser Thr Leu Leu Ser Ala His Ala Pro
            195                 200                 205
```

```
Pro Thr His Lys Arg Leu Thr Ile Pro Lys Gly Leu Pro Leu Ala Val
    210                 215                 220
Lys Ala Gly Leu Met Thr Leu Ile Glu Arg Gln Val Leu Asp Arg Val
225                 230                 235                 240
Cys Gly Pro Glu Leu Asn Ala Ala Arg Gln Ala Leu Gly Leu Ala Pro
                245                 250                 255
Ala Lys Arg Ile Leu Gly Arg Trp Leu His Ser Thr Asp Gly Val Leu
            260                 265                 270
Cys Leu Phe Pro Ser Trp Phe Ala Pro Ala Gln Pro Asp Trp Pro Ala
        275                 280                 285
Asn His Leu Gln Ser Gly Phe Pro Leu Phe Asn Asp Ala Gly Pro Ala
    290                 295                 300
Gln Ala Asp Ala Glu Leu Glu Ala Phe Val Ala Ser Gly Glu Ala Pro
305                 310                 315                 320
Val Val Phe Thr Ala Gly Ser Thr Leu Val Asp Gly Arg Thr Tyr Glu
                325                 330                 335
His Ala Val Thr Gln Val Leu Gln Ala Thr Gly Val Arg Gly Ile Leu
            340                 345                 350
Leu Ala Pro Asp Ala Pro Asp Ala Pro Ala Ala Ser Asp Gly Ala Ala
        355                 360                 365
Leu Leu Lys Arg Arg Tyr Val Pro Leu Ala Ala Leu Leu Pro Arg Cys
    370                 375                 380
Arg Ala Leu Val His His Gly Gly Ile Gly Thr Ala Ser Leu Ala Tyr
385                 390                 395                 400
Ala Ala Gly Val Pro Gln Val Val Thr Pro Phe Ala His Asp Gln Phe
                405                 410                 415
Asp Asn Ala Gln Arg Val Ala Ala Ser Gly Cys Gly Val Arg Leu Asp
            420                 425                 430
Ala Pro Val Arg Gly Glu Pro Leu Ala Arg Ala Leu Ala Gln Val Leu
        435                 440                 445
Gly Asp Ala Ala Met Ala Ala Arg Cys Ala Gln Val Arg Ala Arg Met
    450                 455                 460
Ala Ala Glu Pro Asn Gly Cys Asp Ala Ala Arg Phe Ile Glu Arg
465                 470                 475                 480
Phe Ala Pro Gly Val Ala Ala Arg Arg Ala Gln Pro Ala
                485                 490

<210> SEQ ID NO 9
<211> LENGTH: 426
<212> TYPE: PRT
<213> ORGANISM: Pseudomonas sp.
<220> FEATURE:
<221> NAME/KEY: SITE
<222> LOCATION: (1)..(426)
<223> OTHER INFORMATION: Enyzme E2c

<400> SEQUENCE: 9

Met His Ala Ile Leu Ile Ala Ile Gly Ser Ala Gly Asp Val Phe Pro
1               5                   10                  15
Phe Ile Gly Leu Ala Arg Thr Leu Lys Leu Arg Gly His Arg Val Ser
            20                  25                  30
Leu Cys Thr Ile Pro Val Phe Arg Ala Ala Val Glu Gln His Gly Ile
        35                  40                  45
Glu Phe Val Pro Leu Ser Asp Glu Leu Thr Tyr Arg Arg Thr Met Gly
    50                  55                  60
```

-continued

```
Asp Pro Arg Leu Trp Asp Pro Lys Thr Ser Phe Gly Val Leu Trp Gln
 65                  70                  75                  80

Ala Ile Ala Gly Met Ile Glu Pro Val Tyr Glu Tyr Val Cys Ala Gln
                 85                  90                  95

Arg His Asp Asp Ile Val Val Gly Ser Leu Trp Ala Leu Gly Ala
            100                 105                 110

Arg Ile Ala His Glu Lys Tyr Gly Ile Pro Tyr Leu Ser Val Gln Val
            115                 120                 125

Ser Pro Ser Thr Leu Leu Ser Ala His Leu Pro Pro Val His Pro Arg
130                 135                 140

Phe Asn Val Pro Glu Gln Val Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Val Gly Pro Ala Lys Arg Ile
                180                 185                 190

Phe Thr Gln Trp Met His Ser Pro Gln Gly Val Leu Cys Leu Phe Pro
            195                 200                 205

Ala Trp Phe Ala Pro Pro Gln Gln Asp Trp Pro Gln Pro Leu His Met
210                 215                 220

Thr Gly Phe Pro Leu Phe Asp Gly Ser Val Pro Gly Thr Arg Leu Asp
225                 230                 235                 240

Asp Glu Leu Gln Arg Phe Leu Glu Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
            275                 280                 285

Ala Gly Gln Glu Pro Leu Arg Gly Leu Pro Ser His Val Leu Gln Arg
290                 295                 300

Ser Tyr Val Pro Leu Gly Ala Leu Leu Pro Ala Cys Ala Gly Leu Val
305                 310                 315                 320

His Pro Ala Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
            340                 345                 350

Arg Leu Val Arg Leu Gly Cys Gly Ile Arg Leu Gly Leu Pro Leu Arg
            355                 360                 365

Glu Gln Ala Leu Arg Glu Ser Leu Trp Arg Leu Leu Glu Asp Pro Ala
370                 375                 380

Leu Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                405                 410                 415

Gly Asp Val Arg Trp Leu Lys Ala Ala Ser
            420                 425
```

<210> SEQ ID NO 10
<211> LENGTH: 426
<212> TYPE: PRT
<213> ORGANISM: Pseudomonas sp.
<220> FEATURE:
<221> NAME/KEY: SITE
<222> LOCATION: (1)..(426)
<223> OTHER INFORMATION: Enzyme E2d

<400> SEQUENCE: 10

```
Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
            20                  25                  30

Leu Cys Thr Ile Pro Val Phe Arg Asp Ala Val Glu Gln His Gly Ile
        35                  40                  45

Ala Phe Val Pro Leu Ser Asp Glu Leu Thr Tyr Arg Arg Thr Met Gly
    50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Ser Ala Gln
                85                  90                  95

Arg His Asp Asp Ile Val Val Gly Ser Leu Trp Ala Leu Gly Ala
                100                 105                 110

Arg Ile Ala His Glu Lys Tyr Gly Ile Pro Tyr Leu Ser Ala Gln Val
            115                 120                 125

Ser Pro Ser Thr Leu Leu Ser Ala His Leu Pro Pro Val His Pro Lys
    130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Asn His Val Leu Gln Arg
    290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
            340                 345                 350

Arg Leu Val Arg Leu Gly Cys Gly Met Arg Leu Gly Val Pro Leu Arg
        355                 360                 365

Glu Gln Glu Leu Arg Gly Ala Leu Trp Arg Leu Glu Asp Pro Ala
    370                 375                 380

Met Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                405                 410                 415
```

```
Gly Asp Ala Arg Trp Leu Lys Ala Ala Ser
                420                 425

<210> SEQ ID NO 11
<211> LENGTH: 426
<212> TYPE: PRT
<213> ORGANISM: Pseudomonas sp.
<220> FEATURE:
<221> NAME/KEY: SITE
<222> LOCATION: (1)..(426)
<223> OTHER INFORMATION: Enzyme E2e

<400> SEQUENCE: 11

Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Asp Ala Val Glu Gln His Gly Ile
            35                  40                  45

Ala Phe Val Pro Leu Ser Asp Glu Leu Thr Tyr Arg Arg Thr Met Gly
        50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Ser Ala Gln
                85                  90                  95

Arg His Asp Asp Ile Val Val Gly Ser Leu Trp Ala Leu Gly Ala
                100                 105                 110

Arg Ile Ala His Glu Lys Tyr Gly Ile Pro Tyr Leu Ser Ala Gln Val
            115                 120                 125

Ser Pro Ser Thr Leu Leu Ser Ala His Leu Pro Pro Val His Pro Lys
130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Ala Arg Gly Ile Phe Leu Thr Gly
        275                 280                 285

Ala Gly Gln Glu Pro Leu Arg Gly Leu Pro Asn His Val Leu Gln Arg
290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335
```

```
Pro Gln Val Leu Leu Pro Cys Ala His Asp Gln Phe Asp Asn Ala Glu
            340                 345                 350

Arg Leu Val Arg Leu Gly Cys Gly Met Arg Leu Gly Val Pro Leu Arg
            355                 360                 365

Glu Gln Glu Leu Arg Gly Ala Leu Trp Arg Leu Leu Glu Asp Pro Ala
            370                 375                 380

Met Ala Ala Ala Cys Arg Arg Phe Met Glu Leu Ser Gln Pro His Ser
385                 390                 395                 400

Ile Ala Cys Gly Lys Ala Ala His Val Val Glu Arg Cys His Arg Glu
                405                 410                 415

Gly Asp Ala Arg Trp Leu Lys Ala Ala Ser
            420                 425

<210> SEQ ID NO 12
<211> LENGTH: 323
<212> TYPE: PRT
<213> ORGANISM: Pseudomonas sp.
<220> FEATURE:
<221> NAME/KEY: SITE
<222> LOCATION: (1)..(323)
<223> OTHER INFORMATION: Enzyme 3a

<400> SEQUENCE: 12

Arg Ile Asp Met Gly Val Leu Val Val Leu Phe Asn Pro Gly Asp Asp
1               5                   10                  15

Asp Leu Glu His Leu Gly Glu Leu Ala Ala Phe Pro Gln Leu Arg
            20                  25                  30

Phe Leu Ala Val Asp Asn Ser Pro His Ser Asp Pro Gln Arg Asn Ala
            35                  40                  45

Arg Leu Arg Gly Gln Gly Ile Ala Val Leu His His Gly Asn Arg Gln
        50                  55                  60

Gly Ile Ala Gly Ala Phe Asn Gln Gly Leu Asp Ala Leu Phe Arg Arg
65              70                  75                  80

Gly Val Gln Gly Val Leu Leu Asp Gln Asp Ser Arg Pro Gly Gly
            85                  90                  95

Ala Phe Leu Ala Ala Gln Trp Arg Asn Leu Gln Ala Arg Asn Gly Gln
            100                 105                 110

Ala Cys Leu Leu Gly Pro Arg Ile Phe Asp Arg Gly Asp Arg Arg Phe
            115                 120                 125

Leu Pro Ala Ile His Leu Asp Gly Leu Thr Leu Arg Gln Leu Ser Leu
            130                 135                 140

Asp Gly Leu Thr Thr Pro Gln Arg Thr Ser Phe Leu Ile Ser Ser Gly
145                 150                 155                 160

Cys Leu Leu Thr Arg Glu Ala Tyr Gln Arg Leu Gly His Phe Asp Glu
                165                 170                 175

Glu Leu Phe Ile Asp His Val Asp Thr Glu Tyr Ser Leu Arg Ala Gln
            180                 185                 190

Ala Leu Asp Val Pro Leu Tyr Val Asp Pro Arg Leu Val Leu Glu His
            195                 200                 205

Arg Ile Gly Thr Arg Lys Thr Arg Arg Leu Gly Gly Leu Ser Leu Ser
        210                 215                 220

Ala Met Asn His Ala Pro Leu Arg Arg Tyr Tyr Leu Ala Arg Asn Gly
225                 230                 235                 240

Leu Leu Val Leu Arg Arg Tyr Ala Arg Ser Ser Pro Leu Ala Leu Leu
                245                 250                 255

Ala Asn Leu Pro Thr Leu Thr Gln Gly Leu Ala Val Leu Leu Leu Glu
```

```
                260                 265                 270
Arg Asp Lys Leu Leu Lys Leu Arg Cys Leu Gly Trp Gly Leu Trp Asp
            275                 280                 285

Gly Leu Arg Gly Arg Gly Ala Leu Glu Thr Asn Arg Pro Arg Leu
        290                 295                 300

Leu Lys Arg Leu Ala Gly Pro Ala Val Ala Ser Val Ala Ser Gly Lys
305                 310                 315                 320

Ala Lys Ala

<210> SEQ ID NO 13
<211> LENGTH: 321
<212> TYPE: PRT
<213> ORGANISM: Burkholderia sp.
<220> FEATURE:
<221> NAME/KEY: SITE
<222> LOCATION: (1)..(321)
<223> OTHER INFORMATION: Enzyme 3b

<400> SEQUENCE: 13

Met Thr Ile Leu Gly Ala Leu Val Ile Leu Tyr Asp Pro Thr Asp Glu
1               5                   10                  15

Gln Leu Ser Gly Leu Glu Ala Leu Ala Arg Asp Ser Asp Ala Leu Val
            20                  25                  30

Val Val Asp Asn Thr Pro His Glu His Ala Ala Arg Glu Arg Val
        35                  40                  45

Arg Ala Leu Ser Ala Arg Thr Asn Thr Val Trp Arg His His Gly Asn
50                  55                  60

Arg Gly Gly Val Ala Gly Gly Tyr Asn Ala Gly Leu Ser Val Leu Phe
65                  70                  75                  80

Ala Gln Gly Val Glu Ala Val Ala Leu Phe Asp Gln Asp Ser Thr Val
            85                  90                  95

Pro Ala Gly Tyr Phe Glu Arg Met Arg Glu Ala Cys Ala Gln Leu Gly
        100                 105                 110

Glu Gln Pro Gly Ala His Ala Gly Ala Phe Ile Ala Gly Pro Arg Ile
    115                 120                 125

Tyr Asp Ala Asn Glu Gln Arg Phe Leu Pro Glu Leu Met Thr Ser Gly
130                 135                 140

Val Thr Val Arg Arg Val Arg Val Glu Gly Glu Thr Ala Pro Gln Arg
145                 150                 155                 160

Cys Ala Phe Leu Ile Ser Ser Gly Ser Val Ile Ser Arg Ala Ala Tyr
            165                 170                 175

Ala Arg Leu Gly Arg Phe Asp Glu Ala Leu Phe Ile Asp His Val Asp
        180                 185                 190

Thr Glu Tyr Cys Leu Arg Ala Leu Ala His Asn Val Pro Leu Tyr Val
    195                 200                 205

Val Pro Pro Leu Val Leu Thr His Arg Ile Gly Ala Arg Arg His
210                 215                 220

Lys Val Gly Pro Phe Glu Leu Thr Ala Met His His Gly Trp Leu Arg
225                 230                 235                 240

Arg Tyr Tyr Gly Ala Arg Asn Ala Met Gln Leu Gly Leu Gln Tyr Gly
            245                 250                 255

Leu Arg Phe Pro Val Ala Leu Val Pro Asn Leu Leu Thr Ile Trp Gln
        260                 265                 270

Val Ile Gln Val Val Leu Cys Glu Arg Glu Lys Gly Ala Lys Leu Arg
    275                 280                 285
```

```
Gly Ile Ala Leu Gly Val Leu Asp Gly Leu Phe Gly Arg Leu Gly Ser
290                 295                 300

Phe Asp Asp Ala Arg Ala Gly Ala Ala Arg Glu Pro Val Arg Gln
305                 310                 315                 320

Glu

<210> SEQ ID NO 14
<211> LENGTH: 325
<212> TYPE: PRT
<213> ORGANISM: Pseudomonas sp.
<220> FEATURE:
<221> NAME/KEY: SITE
<222> LOCATION: (1)..(325)
<223> OTHER INFORMATION: Enzyme E3c

<400> SEQUENCE: 14

Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
            20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu Tyr His Gly Asn
50                  55                  60

Arg Gln Gly Ile Ala Gly Ala Phe Asn Gln Gly Leu Asp Thr Leu Phe
65                  70                  75                  80

Arg Arg Gly Leu Gln Gly Val Leu Leu Leu Asp Gln Asp Ser Arg Pro
                85                  90                  95

Gly Gly Ala Phe Leu Ala Ala Gln Trp Arg Asn Leu Gln Ala Cys Asn
            100                 105                 110

Gly Gln Ala Cys Leu Leu Gly Pro Arg Ile Phe Asp Arg Gly Asp Arg
            115                 120                 125

Arg Phe Leu Pro Ala Ile His Leu Asp Gly Leu Ala Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
            195                 200                 205

Glu His Arg Ile Gly Thr Arg Lys Thr Arg Arg Leu Gly Gly Leu Ser
210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
            260                 265                 270

Leu Glu Arg Asp Lys Leu Leu Lys Leu Arg Cys Leu Gly Trp Gly Leu
            275                 280                 285

Trp Asp Gly Leu Arg Gly Arg Gly Gly Ala Leu Glu Arg Asn Arg Pro
290                 295                 300

Arg Leu Leu Lys Arg Leu Ala Gly Pro Ala Val Ala Pro Thr Val Pro
305                 310                 315                 320
```

Gly Lys Ala Lys Ala
            325

<210> SEQ ID NO 15
<211> LENGTH: 325
<212> TYPE: PRT
<213> ORGANISM: Pseudomonas sp.
<220> FEATURE:
<221> NAME/KEY: SITE
<222> LOCATION: (1)..(325)
<223> OTHER INFORMATION: Enzyme E3d

<400> SEQUENCE: 15

Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
                20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu His His Gly Asn
50                  55                  60

Arg Gln Gly Ile Ala Gly Ala Phe Asn Gln Gly Leu Asp Ala Leu Phe
65                  70                  75                  80

Arg Arg Gly Val Gln Gly Val Leu Leu Leu Asp Gln Asp Ser Arg Pro
                85                  90                  95

Gly Gly Ala Phe Leu Ala Ala Gln Trp Arg Asn Leu Gln Ala Arg Asn
                100                 105                 110

Gly Gln Ala Cys Leu Leu Gly Pro Arg Ile Phe Asp Arg Gly Asp Arg
            115                 120                 125

Arg Phe Leu Pro Ala Ile His Leu Asp Gly Leu Thr Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
            195                 200                 205

Glu His Arg Ile Gly Thr Arg Lys Thr Arg Arg Leu Gly Gly Leu Ser
210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
            260                 265                 270

Leu Glu Arg Asp Lys Leu Leu Lys Leu Arg Cys Leu Gly Trp Gly Leu
            275                 280                 285

Trp Asp Gly Leu Arg Gly Arg Gly Ala Leu Glu Arg Asn Arg Pro
290                 295                 300

Arg Leu Leu Lys Arg Leu Ala Gly Pro Ala Val Ala Ser Val Ala Ser
305                 310                 315                 320

Gly Lys Ala Lys Ala
            325

```
<210> SEQ ID NO 16
<211> LENGTH: 422
<212> TYPE: PRT
<213> ORGANISM: Pseudomonas sp.
<220> FEATURE:
<221> NAME/KEY: SITE
<222> LOCATION: (1)..(422)
<223> OTHER INFORMATION: Enzyme E8a

<400> SEQUENCE: 16

Val Ser Thr Thr Ser Leu Cys Pro Ser Ala Thr Arg Glu His Gly Pro
1               5                   10                  15

Gly Ala Lys Arg Val Leu Pro Leu Leu Phe Leu Thr Cys Leu Leu Asp
            20                  25                  30

Ala Ala Gly Val Gly Leu Ile Val Pro Leu Leu Pro Thr Leu Ile Gly
        35                  40                  45

Ser Val Ala Pro Leu Ala Val Arg Asp Ala Ala Thr Trp Gly Ala Ala
    50                  55                  60

Leu Val Met Thr Phe Ala Leu Leu Gln Leu Phe Ser Pro Val Leu
65                  70                  75                  80

Gly Ser Leu Ser Asp Arg Phe Gly Arg Arg Pro Val Leu Val Leu Ala
                85                  90                  95

Met Leu Gly Phe Ala Leu Ser Tyr Leu Leu Ala Leu Ala Asp Ser
            100                 105                 110

Leu Trp Met Leu Phe Leu Gly Arg Ala Leu Ala Gly Leu Thr Gly Ala
        115                 120                 125

Ser Val Ala Thr Ala Met Ala Cys Ala Ala Asp Leu Gly Thr His Gly
    130                 135                 140

Gln Arg Thr Arg His Phe Gly Trp Leu Tyr Ala Gly Leu Ala Leu Gly
145                 150                 155                 160

Met Ile Leu Gly Pro Ala Leu Gly Gly Leu Leu Ala Val His Gly Thr
                165                 170                 175

Thr Leu Pro Leu Leu Leu Ala Ala Gly Leu Cys Leu Leu Asn Ala Leu
            180                 185                 190

Leu Ala Gly Leu Phe Leu Glu Glu Thr Leu Pro Pro Thr Arg Arg Arg
        195                 200                 205

Arg Leu Asp Pro Arg Arg Met Asn Ala Leu Arg Ser Ile Ser Gly Leu
    210                 215                 220

Ala Arg Gln Pro Gly Val Gly Arg Leu Leu Ala Val Leu Ala Leu Val
225                 230                 235                 240

Phe Leu Gly Leu Gln Ala Val Met Val Val Trp Pro Phe Phe Val Ile
                245                 250                 255

Glu Lys Phe His Trp Ser Ser Ala Trp Ile Gly Tyr Ser Leu Ala Leu
            260                 265                 270

Tyr Gly Val Leu Ala Val Leu Ala Gln Thr Leu Gly Val Asn Leu Cys
        275                 280                 285

Lys Arg Arg Leu Asp Asp Ala Arg Leu Leu Arg Leu Gly Leu Ala Leu
    290                 295                 300

Gln Gly Cys Gly Leu Leu Leu Phe Ala Leu Val Asp Ser Ser Phe Trp
305                 310                 315                 320

Leu Val Cys Ala Leu Leu Pro Phe Ala Leu Gly Ser Leu Ala Thr Pro
                325                 330                 335

Ala Met Gln Gly Leu Leu Ser Ala Arg Val Pro Val Asp Arg Gln Gly
            340                 345                 350

Glu Leu Gln Gly Val Leu Ser Ser Leu Met Ser Leu Ala Ala Ile Val
```

```
                    355                 360                 365
Gly Pro Pro Leu Met Ser Gly Leu Phe His Trp Gly Ser Gly Pro Leu
        370                 375                 380

Ala Pro Leu Pro Leu Ala Gly Ala Pro Phe Leu Ala Gly Ala Leu Leu
385                 390                 395                 400

Val Leu Ala Gly Leu Val Leu Ala Trp Gln Leu Arg Pro Thr Gly Glu
                405                 410                 415

Glu Arg Ser Trp Thr Gly
                420

<210> SEQ ID NO 17
<211> LENGTH: 518
<212> TYPE: PRT
<213> ORGANISM: Burkholderia sp.
<220> FEATURE:
<221> NAME/KEY: SITE
<222> LOCATION: (1)..(518)
<223> OTHER INFORMATION: Enzyme E8b

<400> SEQUENCE: 17

Met Ser Ala Asp Gln Ala Gly Val Ala Pro Ala Ala Ala Pro Leu
1               5                   10                  15

Arg Gly Ala Lys Leu Ala Leu Leu Thr Phe Ala Leu Ser Leu Ala Thr
                20                  25                  30

Phe Ile Glu Val Leu Asp Ser Thr Val Ala Asn Val Ala Val Pro Ala
            35                  40                  45

Ile Ser Gly Ser Leu Gly Val Ser Asn Ser Gln Gly Thr Trp Val Ile
        50                  55                  60

Ser Ser Tyr Ser Val Ala Ala Ile Ala Val Pro Leu Thr Gly Trp
65                  70                  75                  80

Leu Ala Arg Arg Val Gly Glu Leu Arg Leu Phe Val Ala Ser Val Ile
                85                  90                  95

Leu Phe Thr Leu Thr Ser Leu Leu Cys Gly Leu Ala Arg Asp Leu Glu
            100                 105                 110

Val Leu Val Ala Cys Arg Ala Leu Gln Gly Leu Phe Ser Gly Pro Met
        115                 120                 125

Val Pro Leu Ser Gln Thr Ile Leu Met Arg Ala Phe Pro Pro Ala Arg
    130                 135                 140

Arg Thr Leu Ala Leu Ala Leu Trp Gly Met Thr Val Leu Leu Ala Pro
145                 150                 155                 160

Ile Phe Gly Pro Val Val Gly Gly Trp Leu Ile Asp Asn Phe Ser Trp
                165                 170                 175

Pro Trp Ile Phe Leu Ile Asn Leu Pro Ile Gly Leu Phe Ser Phe Ala
            180                 185                 190

Val Cys Thr Leu Met Leu Arg Pro Gln Ala Gln Arg Gly Glu Ala Ser
        195                 200                 205

Pro Ile Asp Ala Pro Gly Ile Val Leu Val Ile Gly Val Gly Ser
    210                 215                 220

Leu Gln Ala Met Leu Asp Leu Gly His Asp Arg Gly Trp Phe Asp Ser
225                 230                 235                 240

Pro Leu Ile Thr Ala Leu Ala Ile Ala Ala Gly Val Ser Leu Val Ser
                245                 250                 255

Leu Leu Ile Trp Glu Leu Gly Glu Ala His Pro Val Val Asp Leu Ser
            260                 265                 270

Leu Phe Arg Glu Arg Thr Phe Thr Phe Cys Val Val Ile Ile Ser Leu
        275                 280                 285
```

```
Gly Met Met Ser Phe Ser Val Gly Val Val Phe Pro Leu Trp Leu
            290                 295                 300

Gln Ala Val Met Gly Tyr Thr Ala Tyr Gln Ala Gly Leu Ala Thr Ala
305                 310                 315                 320

Ser Met Gly Val Leu Ala Leu Val Phe Ser Ile Leu Val Gly Leu Tyr
                325                 330                 335

Ala Ser Arg Val Asp Ala Arg Val Leu Val Thr Phe Gly Phe Gly Val
                340                 345                 350

Phe Ala Ala Val Met Trp Trp Ser Thr His Phe Thr Leu Ser Met Thr
                355                 360                 365

Phe Ala Gln Val Val Thr Pro Arg Leu Ile Gln Gly Met Gly Leu Pro
                370                 375                 380

Cys Phe Phe Ile Pro Leu Thr Ala Ala Thr Leu Ser Arg Val Pro Asp
385                 390                 395                 400

Glu Lys Leu Ala Ala Ala Ser Ser Leu Ser Asn Phe Leu Arg Thr Leu
                405                 410                 415

Ser Ala Ala Phe Gly Thr Ala Leu Ser Val Thr Trp Trp Asp Asn Arg
                420                 425                 430

Ala Thr Tyr His Tyr Ala Val Ser Gln Ser Val Thr Arg Ala Ser
                435                 440                 445

Glu Asn Thr Gln Arg Tyr Val Asp Ala Leu His Ala Met Gly Leu His
450                 455                 460

Gly Ala Arg Glu Leu Ser Ser Leu His Gln Val Val Arg Gln Gln Ala
465                 470                 475                 480

Tyr Met Met Ala Thr Asn Asp Met Phe Tyr Met Ala Ser Ala Thr Cys
                485                 490                 495

Leu Leu Leu Ala Gly Leu Met Trp Leu Thr Arg Pro Lys Arg Gly Ala
                500                 505                 510

Ala Ala Ala Leu Gly His
            515

<210> SEQ ID NO 18
<211> LENGTH: 553
<212> TYPE: PRT
<213> ORGANISM: Burkholderia sp.
<220> FEATURE:
<221> NAME/KEY: SITE
<222> LOCATION: (1)..(553)
<223> OTHER INFORMATION: Enzyme E8c

<400> SEQUENCE: 18

Met Arg Ala Arg Ala Arg Arg Ala Ser Arg Cys Gly Arg Asn Glu
1               5                   10                  15

Arg Asn Gly Pro Gln Arg Asp Thr Gly Lys Gln Glu Gly Arg Ile Ile
                20                  25                  30

Arg Met Thr Gln Thr Ala Thr Gln Ala Ala Thr Arg Ala Met Ile Ala
            35                  40                  45

Thr Gly Ser Arg Ala Ala Arg Arg Leu Ala Ala Ala Leu Ala Trp
        50                  55                  60

Ala Leu Ala Gly Cys Val Pro Ser Gly Phe Glu Pro Ala Leu Ala Pro
65                  70                  75                  80

Arg Thr Pro Gly Asp Asp Ala Leu Ala His Thr Ala Gly Gly Ala Ala
                85                  90                  95

His Gly Ala Trp Pro Ser Pro Asp Trp Val Arg Gln Leu Gly Asp Pro
            100                 105                 110
```

```
Gln Leu Asp Ala Leu Val Asp Glu Ala Leu Arg Gln Asn Pro Thr Leu
            115                 120                 125
Gln Ala Ala Gln Ala Arg Ile Gly Val Ala Gln Ser Gln Leu Gln Gln
        130                 135                 140
Phe Glu Ser Leu Thr Gly Leu Thr Ala Thr Ala Gly Ala Ser Leu Ser
145                 150                 155                 160
Lys Ala His Val Pro Arg Ser Gly Thr Ile Asn Thr Thr Phe Asn
                165                 170                 175
Gly Leu Pro Val Ser Pro Leu Val Gly Glu Ser Val Val Ser Ser
            180                 185                 190
Ser Ser Leu Phe Val Gly Leu Asn Tyr Gln Leu Asp Leu Trp Gly Lys
        195                 200                 205
Asn Ala Ala Thr Arg Gly Leu Leu Ser Met Arg Asp Ala Ala Arg
210                 215                 220
Val Glu Ala Glu Gln Ala Arg Leu Ala Leu Ser Val Ala Ile Val Thr
225                 230                 235                 240
Leu Tyr Gly Glu Leu Asp Arg Ala Tyr Ala Leu Arg Glu Leu Leu Gln
            245                 250                 255
Gln Lys Arg Arg Ala Ser Glu Gln Val Glu Thr Val Leu Arg Glu Arg
        260                 265                 270
Ala Ala Arg Gly Ile Asp Asn Gly Tyr Asp Ala Asp Asp Ala Ala Leu
        275                 280                 285
Lys Arg Gly Lys Leu Leu Glu Gln Leu Ala Leu Thr Asp Glu Gln Ile
        290                 295                 300
Gln Leu Gln Lys Leu Gln Leu Gly Val Leu Ser Gly Arg Gly Pro Glu
305                 310                 315                 320
Arg Gly Leu Ser Leu Ala Arg Pro Lys Leu Ala Pro Leu Ala Asp Ala
            325                 330                 335
Pro Leu Pro Ala Arg Leu Pro Ala Gly Leu Leu Gly Arg Arg Pro Asp
            340                 345                 350
Ile Val Ala Ala Arg Leu Arg Val Glu Ala Ala Tyr Ala Ala Ile Asp
                355                 360                 365
Gly Thr Arg Ala Ser Phe Tyr Pro Asp Val Asn Leu Ala Ala Leu Gly
370                 375                 380
Gly Leu Phe Ala Leu Thr Pro Ala Ser Leu Phe Lys His Asp Ala Leu
385                 390                 395                 400
Gly Gly Ser Ile Gly Pro Ala Leu Ser Leu Pro Ile Phe Asp Arg Gly
                405                 410                 415
Arg Leu Lys Ala Lys Leu Gly Gly Asp Val Ala Asn Ala Asp Val Ala
            420                 425                 430
Leu Ala Leu Tyr Asn Gln Thr Val Asp Ala Ala Leu Gly Glu Val Ala
        435                 440                 445
Arg Gln Leu Thr Ser Leu Ser Thr Val Asp Ala Leu Leu Glu Ala Gln
    450                 455                 460
Gln Gln Ala Val Arg Ser Ala Gln Arg Met Val Ala Leu Ala Gln Asp
465                 470                 475                 480
Arg His Arg Arg Gly Met Gly Met Arg Lys Asp Val Asn Val Ala Lys
            485                 490                 495
Leu Thr Leu Leu Asp Glu Arg Ala His Val Ile Glu Leu Gln Ala Arg
        500                 505                 510
Arg Arg Thr Leu Arg Val Gly Leu Ile Gly Ala Leu Gly Gly Gly Phe
    515                 520                 525
Asp Ala Arg Pro Ala Gly Gly Ala Pro Leu Ala Gln Gly Lys Pro Phe
```

Ala Ala Ala Ser Asp Arg Pro Pro Asp
545                 550

<210> SEQ ID NO 19
<211> LENGTH: 466
<212> TYPE: PRT
<213> ORGANISM: Burkholderia sp.
<220> FEATURE:
<221> NAME/KEY: SITE
<222> LOCATION: (1)..(466)
<223> OTHER INFORMATION: Enzyme E8d

<400> SEQUENCE: 19

Met Arg Pro Glu Ala Thr Asp Thr Arg Arg His Arg Gln Arg His
1               5                   10                  15

Leu His Arg Val His Glu Arg Phe Asn Arg His Arg Pro Arg Ala Ser
                20                  25                  30

Lys Pro Val Gly Pro Ile Arg Asp Gly Leu Arg Ala Gly Pro Ala Val
            35                  40                  45

Ala Gly Arg Arg His Arg His His Ala Arg Glu Asp Leu Glu Arg Tyr
        50                  55                  60

Arg His Arg Tyr Pro Ala Arg Glu Gly Ala His Arg Ser Gly Arg Pro
65                  70                  75                  80

Arg Arg Arg Ala Arg Ala Arg Ala Gly Ala Arg Ala Arg Ile Ala
                85                  90                  95

Ser Ala Ala Gly Ser Arg Gly Asp Ala Arg Arg Ala Pro Arg Asp Ala
                100                 105                 110

Pro Pro Ala Leu Arg Ala Val Leu Arg Ala Gly Ala Gly Arg Ala
            115                 120                 125

Asp Arg Gly Ala Leu Leu Val Arg Arg Ala Leu Gln Arg Gly Asp
        130                 135                 140

Gly Arg Arg Val Arg Gly Arg Gln Arg Gly Ala Asp Arg Arg Ala Asp
145                 150                 155                 160

Pro Gly Asp Gly Asp Arg Arg Ala Gly Gly His Ala Ala Gly Glu
                165                 170                 175

Gly Gly Ala Gly Ala Gly Glu Ala Arg Arg Gly Arg Val Gly Gly
            180                 185                 190

Val Arg Ala Gly Ala Gly Ala Arg Ala Gly Gly Ala Ala Gly Gly
        195                 200                 205

Glu His Ala Ala Leu Asp Gly Asp Val Arg Gly Asp Gly Glu Gly Ala
210                 215                 220

Arg Gly Gly Pro Glu Ala Cys Ala Ala Gly Val Ser Gly Gly Thr Gly
225                 230                 235                 240

Ala Ala Lys Val Val Ala Gly Glu Arg Ala Gly Ala Gly Gly Gly
                245                 250                 255

Ala Gly Ala Ala Gly Gly Gly Ala Arg Ala Gly Gln Arg Ala Ala Gly
                260                 265                 270

Arg Ala Glu Pro Gly Gly Ala Ala Gly Gly Arg Ala Val Gln Ala Gly
            275                 280                 285

Val Pro Glu Pro Glu Ala His Asp Asp Arg Val Ala Gly Gly Arg His
        290                 295                 300

Gly Arg Ser Ala Val Gly Ala Asp Arg Ser Ala Gly Gly Ala Gly Gly
305                 310                 315                 320

Ala Ala Asp Val Gly Gly Ala Val Ala Ala Gly Val Gly Gly Gly Glu
                325                 330                 335

-continued

```
Leu Gln Gly Arg Ala Asp Pro Ala His Ala Gly Gly Pro Ala Gly Ala
            340                 345                 350

Ala Arg Ile Gly Pro Val Arg Ala Gly Asp Val Pro Arg Pro Gly
            355                 360                 365

Gly Gly Gly Leu Gly Gly His Gly Gln Arg Val Leu Asp Ala Ala Val
370                 375                 380

Ala Glu Arg Gly Gly Glu Leu Asp Gln Gly Ala Ala Pro Ala Gly
385                 390                 395                 400

Gly Asp Leu Ala Gly Ala Val Gly Ala Gly Ala Pro Ala Ala Gly
                405                 410                 415

Gly Ala Val Asp Ala Arg Asp Gly Asp Glu Gly Ala Trp Arg Pro
            420                 425                 430

Pro Ala Arg Arg Arg Arg Ala Ala Gly Ala Ala His Ala Gly Ala
            435                 440                 445

Arg Ser Ala Gly Gly Arg Gly Arg Gly Arg Gly Phe Gly Ser Asp Ser
    450                 455                 460

Gly Glu
465

<210> SEQ ID NO 20
<211> LENGTH: 559
<212> TYPE: PRT
<213> ORGANISM: Pseudomonas sp.
<220> FEATURE:
<221> NAME/KEY: SITE
<222> LOCATION: (1)..(559)
<223> OTHER INFORMATION: Enzyme E9a

<400> SEQUENCE: 20

Met Ser Asn Lys Asn Asn Asp Glu Leu Gln Arg Gln Ala Ser Glu Asn
1               5                   10                  15

Thr Met Gly Leu Asn Pro Val Ile Gly Ile Arg Arg Lys Asp Leu Leu
            20                  25                  30

Ser Ser Ala Arg Thr Val Leu Arg Gln Ala Val Arg Gln Pro Leu His
        35                  40                  45

Ser Ala Lys His Val Ala His Phe Gly Leu Glu Leu Lys Asn Val Leu
    50                  55                  60

Leu Gly Lys Ser Ser Leu Ala Pro Asp Ser Asp Asp Arg Arg Phe Asn
65                  70                  75                  80

Asp Pro Ala Trp Ser Asn Asn Pro Leu Tyr Arg Arg Tyr Leu Gln Thr
                85                  90                  95

Tyr Leu Ala Trp Arg Lys Glu Leu Gln Asp Trp Val Ser Ser Asp
            100                 105                 110

Leu Ser Pro Gln Asp Ile Ser Arg Gly Gln Phe Val Ile Asn Leu Met
        115                 120                 125

Thr Glu Ala Met Ala Pro Thr Asn Thr Leu Ser Asn Pro Ala Ala Val
    130                 135                 140

Lys Arg Phe Phe Glu Thr Gly Gly Lys Ser Leu Leu Asp Gly Leu Ser
145                 150                 155                 160

Asn Leu Ala Lys Asp Met Val Asn Asn Gly Gly Met Pro Ser Gln Val
                165                 170                 175

Asn Met Asp Ala Phe Glu Val Gly Lys Asn Leu Gly Thr Ser Glu Gly
            180                 185                 190

Ala Val Val Tyr Arg Asn Asp Val Leu Glu Leu Ile Gln Tyr Ser Pro
        195                 200                 205
```

-continued

```
Ile Thr Glu Gln Val His Ala Arg Pro Leu Leu Val Pro Pro Gln
    210                 215                 220

Ile Asn Lys Phe Tyr Val Phe Asp Leu Ser Pro Glu Lys Ser Leu Ala
225                 230                 235                 240

Arg Phe Cys Leu Arg Ser Gln Gln Thr Phe Ile Ile Ser Trp Arg
                245                 250                 255

Asn Pro Thr Lys Ala Gln Arg Glu Trp Gly Leu Ser Thr Tyr Ile Asp
                260                 265                 270

Ala Leu Lys Glu Ala Val Asp Ala Val Leu Ser Ile Thr Gly Ser Lys
                275                 280                 285

Asp Leu Asn Met Leu Gly Ala Cys Ser Gly Gly Ile Thr Cys Thr Ala
    290                 295                 300

Leu Val Gly His Tyr Ala Ala Leu Gly Glu Asn Lys Val Asn Ala Leu
305                 310                 315                 320

Thr Val Leu Val Ser Val Leu Asp Thr Thr Met Asp Asn Gln Val Ala
                325                 330                 335

Leu Phe Val Asp Glu Gln Thr Leu Glu Ala Ala Lys Arg His Ser Tyr
                340                 345                 350

Gln Ala Gly Val Leu Glu Gly Ser Glu Met Ala Lys Val Phe Ala Trp
                355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Ser Asn Pro Leu Thr Arg Pro Asp Ala Leu Lys Val Cys Gly Thr
                420                 425                 430

Ala Ile Asp Leu Lys Gln Val Lys Cys Asp Ile Tyr Ser Leu Ala Gly
                435                 440                 445

Thr Asn Asp His Ile Thr Pro Trp Pro Ser Cys Tyr Arg Ser Ala His
    450                 455                 460

Leu Phe Gly Gly Lys Ile Glu Phe Val Leu Ser Asn Ser Gly His Ile
465                 470                 475                 480

Gln Ser Ile Leu Asn Pro Gly Asn Pro Lys Ala Arg Phe Met Thr
                485                 490                 495

Gly Ala Asp Arg Pro Gly Asp Pro Val Ala Trp Gln Glu Asn Ala Ile
                500                 505                 510

Lys His Ala Asp Ser Trp Trp Leu His Trp Gln Ser Trp Leu Gly Glu
    515                 520                 525

Arg Ala Gly Ala Leu Lys Lys Ala Pro Thr Arg Leu Gly Asn Arg Thr
530                 535                 540

Tyr Ala Ala Gly Glu Ala Ser Pro Gly Thr Tyr Val His Glu Arg
545                 550                 555
```

<210> SEQ ID NO 21
<211> LENGTH: 560
<212> TYPE: PRT
<213> ORGANISM: Pseudomonas sp.
<220> FEATURE:
<221> NAME/KEY: SITE
<222> LOCATION: (1)..(560)
<223> OTHER INFORMATION: Enzyme E9b

<400> SEQUENCE: 21

Met Thr Asp Lys Pro Ala Lys Gly Ser Thr Thr Leu Pro Ala Thr Arg

-continued

```
1               5                   10                  15
Met Asn Val Gln Asn Ala Ile Leu Gly Leu Arg Gly Arg Asp Leu Leu
                20                  25                  30

Ser Thr Leu Arg Asn Val Gly Arg His Gly Leu Arg His Pro Leu His
                35                  40                  45

Thr Ala His His Leu Leu Ala Leu Gly Gly Gln Leu Gly Arg Val Met
            50                  55                  60

Leu Gly Asp Thr Pro Tyr Gln Pro Asn Pro Arg Asp Ala Arg Phe Ser
65                  70                  75                  80

Asp Pro Thr Trp Ser Gln Asn Pro Phe Tyr Arg Arg Gly Leu Gln Ala
                85                  90                  95

Tyr Leu Ala Trp Gln Lys Gln Thr Arg Gln Trp Ile Asp Glu Ser His
                100                 105                 110

Leu Asn Asp Asp Arg Ala Arg Ala His Phe Leu Phe Asn Leu Ile
                115                 120                 125

Asn Asp Ala Leu Ala Pro Ser Asn Ser Leu Leu Asn Pro Gln Ala Val
130                 135                 140

Lys Gly Leu Phe Asn Thr Gly Gly Gln Ser Leu Val Arg Gly Val Ala
145                 150                 155                 160

His Leu Leu Asp Asp Leu Arg His Asn Asp Gly Leu Pro Arg Gln Val
                165                 170                 175

Asp Glu Arg Ala Phe Glu Val Gly Val Asn Leu Ala Ala Thr Pro Gly
                180                 185                 190

Ala Val Val Phe Arg Asn Glu Leu Leu Glu Leu Ile Gln Tyr Ser Pro
                195                 200                 205

Met Ser Glu Lys Gln His Ala Arg Pro Leu Leu Val Val Pro Pro Gln
                210                 215                 220

Ile Asn Arg Phe Tyr Ile Phe Asp Leu Ser Ala Thr Asn Ser Phe Val
225                 230                 235                 240

Gln Tyr Met Leu Lys Ser Gly Leu Gln Val Phe Met Val Ser Trp Ser
                245                 250                 255

Asn Pro Asp Pro Arg His Arg Glu Trp Gly Leu Ser Ser Tyr Val Gln
                260                 265                 270

Ala Leu Glu Glu Ala Leu Asn Ala Cys Arg Ser Ile Ser Gly Asn Arg
                275                 280                 285

Asp Pro Asn Leu Met Gly Ala Cys Ala Gly Gly Leu Thr Met Ala Ala
                290                 295                 300

Leu Gln Gly His Leu Gln Ala Lys Lys Gln Leu Arg Arg Val Arg Ser
305                 310                 315                 320

Ala Thr Tyr Leu Val Ser Leu Leu Asp Ser Lys Phe Glu Ser Pro Ala
                325                 330                 335

Ser Leu Phe Ala Asp Glu Gln Thr Ile Glu Ala Ala Lys Arg Arg Ser
                340                 345                 350

Tyr Gln Arg Gly Val Leu Asp Gly Gly Glu Val Ala Arg Ile Phe Ala
                355                 360                 365

Trp Met Arg Pro Asn Asp Leu Ile Trp Asn Tyr Trp Val Asn Asn Tyr
                370                 375                 380

Leu Leu Gly Lys Thr Pro Pro Ala Phe Asp Ile Leu Tyr Trp Asn Ala
385                 390                 395                 400

Asp Ser Thr Arg Leu Pro Ala Ala Leu His Gly Asp Leu Leu Glu Phe
                405                 410                 415

Phe Lys Leu Asn Pro Leu Thr Tyr Ala Ser Gly Leu Glu Val Cys Gly
                420                 425                 430
```

```
Thr Pro Ile Asp Leu Gln Gln Val Asn Ile Asp Ser Phe Thr Val Ala
    435                 440                 445

Gly Ser Asn Asp His Ile Thr Pro Trp Asp Ala Val Tyr Arg Ser Ala
450                 455                 460

Leu Leu Leu Gly Gly Glu Arg Arg Phe Val Leu Ala Asn Ser Gly His
465                 470                 475                 480

Ile Gln Ser Ile Ile Asn Pro Pro Gly Asn Pro Lys Ala Tyr Tyr Leu
                485                 490                 495

Ala Asn Pro Lys Leu Ser Ser Asp Pro Arg Ala Trp Phe His Asp Ala
                500                 505                 510

Lys Arg Ser Glu Gly Ser Trp Trp Pro Leu Trp Leu Trp Ile Thr
                515                 520                 525

Ala Arg Ser Gly Leu Leu Lys Ala Pro Arg Thr Glu Leu Gly Asn Ala
        530                 535                 540

Thr Tyr Pro Leu Leu Gly Pro Ala Pro Gly Thr Tyr Val Leu Thr Arg
545                 550                 555                 560
```

<210> SEQ ID NO 22
<211> LENGTH: 295
<212> TYPE: PRT
<213> ORGANISM: Pseudomonas sp.
<220> FEATURE:
<221> NAME/KEY: SITE
<222> LOCATION: (1)..(295)
<223> OTHER INFORMATION: Enzyme 10a

<400> SEQUENCE: 22

```
Met Arg Pro Glu Ile Ala Val Leu Asp Ile Gln Gly Gln Tyr Arg Val
1               5                   10                  15

Tyr Thr Glu Phe Tyr Arg Ala Asp Ala Ala Glu Asn Thr Ile Ile Leu
            20                  25                  30

Ile Asn Gly Ser Leu Ala Thr Thr Ala Ser Phe Ala Gln Thr Val Arg
        35                  40                  45

Asn Leu His Pro Gln Phe Asn Val Val Leu Phe Asp Gln Pro Tyr Ser
    50                  55                  60

Gly Lys Ser Lys Pro His Asn Arg Gln Glu Arg Leu Ile Ser Lys Glu
65                  70                  75                  80

Thr Glu Ala His Ile Leu Leu Glu Leu Ile Glu His Phe Gln Ala Asp
                85                  90                  95

His Val Met Ser Phe Ser Trp Gly Gly Ala Ser Thr Leu Leu Ala Leu
            100                 105                 110

Ala His Gln Pro Arg Tyr Val Lys Lys Ala Val Val Ser Ser Phe Ser
        115                 120                 125

Pro Val Ile Asn Glu Pro Met Arg Asp Tyr Leu Asp Arg Gly Cys Gln
    130                 135                 140

Tyr Leu Ala Ala Cys Asp Arg Tyr Gln Val Gly Asn Leu Val Asn Asp
145                 150                 155                 160

Thr Ile Gly Lys His Leu Pro Ser Leu Leu Lys Arg Phe Asn Tyr Arg
                165                 170                 175

His Val Ser Ser Leu Asp Ser His Glu Tyr Ala Gln Met His Phe His
            180                 185                 190

Ile Asn Gln Val Leu Glu His Asp Leu Glu Arg Ala Leu Gln Gly Ala
        195                 200                 205

Arg Asn Ile Asn Ile Pro Val Leu Phe Ile Asn Gly Glu Arg Asp Glu
    210                 215                 220
```

```
Tyr Thr Thr Val Glu Asp Ala Arg Gln Phe Ser Lys His Val Gly Arg
225                 230                 235                 240

Ser Gln Phe Ser Val Ile Arg Asp Ala Gly His Phe Leu Asp Met Glu
                245                 250                 255

Asn Lys Thr Ala Cys Glu Asn Thr Arg Ser Val Met Leu Gly Phe Leu
            260                 265                 270

Lys Pro Thr Val Arg Glu Pro Arg Gln Arg Tyr Gln Pro Val Gln Gln
        275                 280                 285

Gly Gln His Ala Leu Ala Ile
    290                 295

<210> SEQ ID NO 23
<211> LENGTH: 300
<212> TYPE: PRT
<213> ORGANISM: Pseudomonas sp.
<220> FEATURE:
<221> NAME/KEY: SITE
<222> LOCATION: (1)..(300)
<223> OTHER INFORMATION: Enzyme 10b

<400> SEQUENCE: 23

Met Arg Pro Glu Thr Ala Ile Ile Glu Ile His Gly Gln Tyr Arg Ile
1               5                   10                  15

His Thr Glu Phe Tyr Gly Asn Pro Ala Ala Gln Gln Thr Ile Ile Leu
            20                  25                  30

Val Asn Gly Ser Leu Ser Thr Thr Ala Ser Phe Ala Gln Thr Val Lys
        35                  40                  45

Tyr Leu Gln Pro His Tyr Asn Val Val Leu Tyr Asp Gln Pro Tyr Ala
50                  55                  60

Gly Gln Ser Lys Pro His Asn Glu Asn His Thr Pro Ile Ser Lys Glu
65                  70                  75                  80

Cys Glu Ala Arg Ile Leu Leu Glu Leu Ile Glu Arg Phe Arg Ala Glu
                85                  90                  95

Val Val Met Ser Phe Ser Trp Gly Gly Val Ala Thr Leu Leu Ala Leu
            100                 105                 110

Ala Gln Arg Pro Gly Arg Ile Arg Arg Ala Val Val Asn Ser Phe Ser
        115                 120                 125

Pro Gln Leu Asn Pro Ala Met Leu Asp Tyr Leu His Arg Gly Leu Asp
    130                 135                 140

Tyr Leu Ala Ala Cys Asp Arg Thr Gln Ile Gly Asn Leu Val Asn Glu
145                 150                 155                 160

Thr Ile Gly Arg Tyr Leu Pro Gln Leu Phe Lys Arg Tyr Asn Phe Arg
                165                 170                 175

His Val Ser Ser Leu Asp Glu His Glu Tyr His Gln Met His Phe His
            180                 185                 190

Ile Arg Glu Val Leu Arg Leu Asn Ala Asp Ser Tyr Thr Glu Ser Phe
        195                 200                 205

Ala Gly Ile Glu Ile Pro Met Leu Phe Met Asn Gly Glu Leu Asp Ile
210                 215                 220

Tyr Thr Thr Pro His Glu Ala Arg Gln Phe Gly Gln Leu Ile Arg Gly
225                 230                 235                 240

Ala Glu Phe His Thr Ile Arg Asn Ala Gly His Phe Ile Asp Val Glu
                245                 250                 255

His Lys Ala Ala Trp Gln Gln Thr Gln Asp Ala Leu Leu Ala Phe Leu
            260                 265                 270
```

```
Arg Pro Gln Arg Thr Gln Pro Leu Asn Pro Ile Tyr Arg Pro Gln Pro
        275                 280                 285

Asn Gly Ala Ser Val Pro Leu Ala Ala Leu Ala Ser
    290                 295                 300
```